US011179657B2

(12) United States Patent
Weston et al.

(10) Patent No.: US 11,179,657 B2
(45) Date of Patent: Nov. 23, 2021

(54) FILTRATION CONTAINER ASSEMBLIES AND METHODS

(71) Applicant: GRAYL Inc., Seattle, WA (US)

(72) Inventors: Nancie Weston, Camano Island, WA (US); Travis Merrigan, Bremerton, WA (US); Michael Bargiel, Phoenix, AZ (US)

(73) Assignee: GRAYL Inc., Seattle, WA (US)

( * ) Notice: Subject to any disclaimer, the term of this patent is extended or adjusted under 35 U.S.C. 154(b) by 0 days.

(21) Appl. No.: 16/927,609

(22) Filed: Jul. 13, 2020

(65) Prior Publication Data

US 2020/0338480 A1  Oct. 29, 2020

Related U.S. Application Data

(63) Continuation of application No. 13/926,496, filed on Jun. 25, 2013, now Pat. No. 10,710,007.
(Continued)

(51) Int. Cl.
 *B01D 29/00* (2006.01)
 *B01D 33/01* (2006.01)
(Continued)

(52) U.S. Cl.
CPC ......... *B01D 29/0072* (2013.01); *B01D 33/01* (2013.01); *B01D 33/0116* (2013.01);
(Continued)

(58) Field of Classification Search
CPC .... B01D 33/01; B01D 33/0116; B01D 33/42; B01D 2313/20; B01D 29/0072;
(Continued)

(56) References Cited

U.S. PATENT DOCUMENTS 2,629,376 A  2/1953 Gallice et al.
2,882,899 A  4/1959 Nogier et al.
(Continued)

FOREIGN PATENT DOCUMENTS

CN      104665434      6/2015
KR  20-1984-0000820 Y1  5/1984
(Continued)

OTHER PUBLICATIONS

International Preliminary Report on Patentability and Written Opinion dated Dec. 31, 2014, issued in corresponding International Application No. PCT/US2013/047686, filed Jun. 25, 2013, 13 pages.
(Continued)

*Primary Examiner* — Patrick Orme
(74) *Attorney, Agent, or Firm* — Polsinelli PC

(57) ABSTRACT

A filtration container assembly generally includes an outer container having a first end and a second end and defining an inner cavity, and a plunging assembly configured to be received within the outer container inner cavity, wherein the plunging assembly includes an inner sleeve having a first end and a second end and an outer wall defining an inner bore, wherein the outer wall is continuous from the first end to the second end, and a filtration assembly coupled to the inner sleeve at the second end.

20 Claims, 30 Drawing Sheets

Related U.S. Application Data

(60) Provisional application No. 61/826,460, filed on May 22, 2013, provisional application No. 61/675,267, filed on Jul. 24, 2012, provisional application No. 61/664,073, filed on Jun. 25, 2012.

(51) Int. Cl.
*A47J 31/20* (2006.01)
*A47J 31/00* (2006.01)
*B01D 33/42* (2006.01)
*C02F 1/00* (2006.01)
*A61M 5/315* (2006.01)

(52) U.S. Cl.
CPC .............. *B01D 33/42* (2013.01); *A47J 31/005* (2013.01); *A47J 31/20* (2013.01); *A61M 5/31513* (2013.01); *B01D 2313/20* (2013.01); *B01L 2300/0681* (2013.01); *B01L 2400/0478* (2013.01); *C02F 1/002* (2013.01)

(58) Field of Classification Search
CPC .............. C02F 1/002; B01L 2300/0681; B01L 2400/0478; A47J 31/005; A47J 31/20; A61M 5/31513
See application file for complete search history.

(56) References Cited

U.S. PATENT DOCUMENTS

| | | | |
|---|---|---|---|
| 3,319,577 A | 5/1967 | Herreshoff | |
| 3,752,604 A | 8/1973 | Dorn | |
| 3,954,614 A | 5/1976 | Wright | |
| 3,955,634 A | 5/1976 | Slator et al. | |
| 4,151,092 A * | 4/1979 | Grimm | C02F 1/003 210/256 |
| 4,189,385 A | 2/1980 | Greenspan | |
| 5,494,410 A | 2/1996 | Maier-Laxhuber et al. | |
| 5,549,573 A | 8/1996 | Waskonig | |
| 7,790,117 B2 | 9/2010 | Ellis et al. | |
| 8,177,968 B2 | 5/2012 | Wang | |
| 8,216,462 B2 | 7/2012 | O'Brien et al. | |
| 8,641,416 B2 * | 2/2014 | Leiner | A61C 5/62 433/90 |
| 2005/0000886 A1 | 1/2005 | Reynolds et al. | |
| 2006/0151381 A1 | 7/2006 | Wennerstrom | |
| 2007/0284300 A1 | 12/2007 | Bidlingmeyer et al. | |
| 2011/0168644 A1 | 7/2011 | Harris | |
| 2013/0001143 A1 * | 1/2013 | Nelson | A23L 2/72 210/136 |
| 2013/0015136 A1 * | 1/2013 | Bennett | B82Y 30/00 210/653 |

FOREIGN PATENT DOCUMENTS

| | | |
|---|---|---|
| KR | 20-2009-0011222 U | 11/2009 |
| KR | 10-2011-0133745 A | 12/2011 |

OTHER PUBLICATIONS

International Search Report and Written Opinion dated Oct. 15, 2013, issued in corresponding International Application No. PCT/US2013/047686, filed Jun. 25, 2013, 15 pages.

Office Action dated Nov. 4, 2015, issued in corresponding Chinese Application No. 201380044454.2 filed Jun. 25, 2013, 17 pages.

* cited by examiner

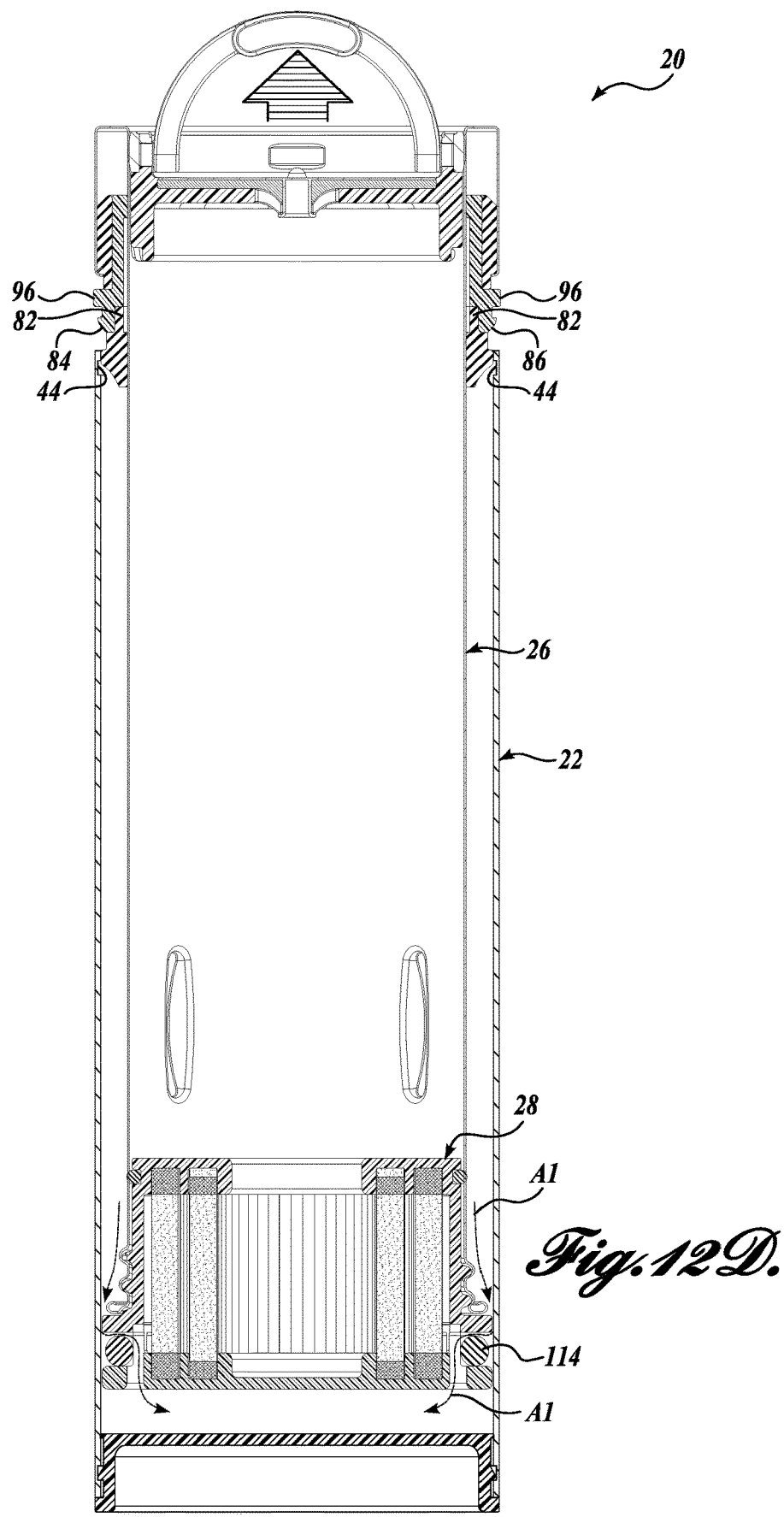

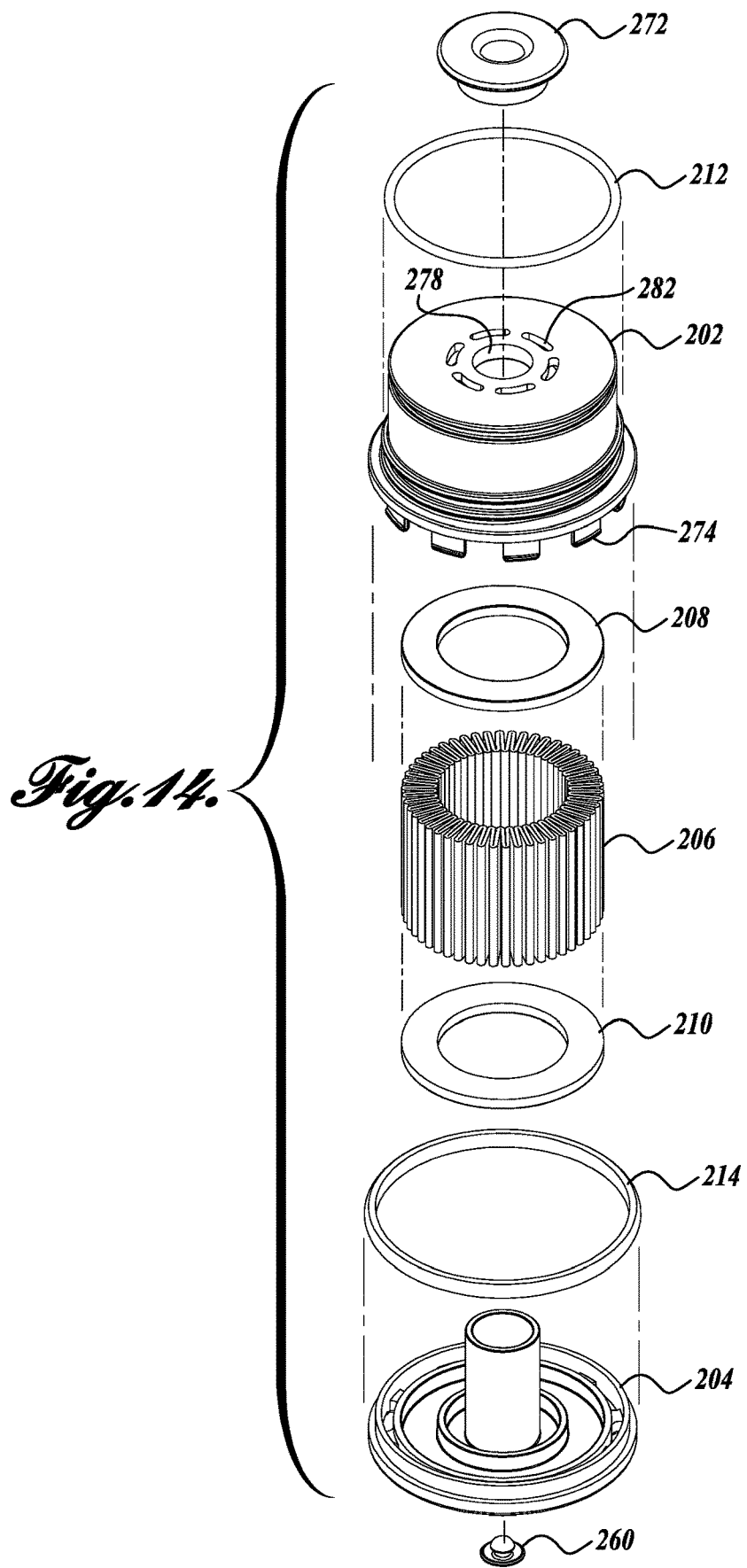

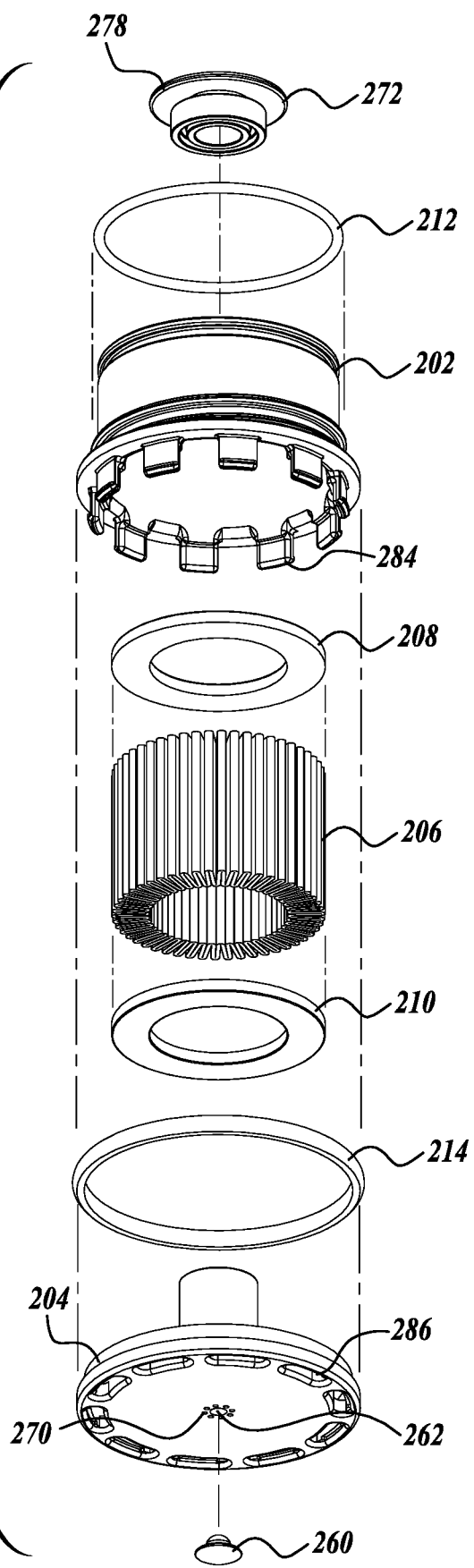

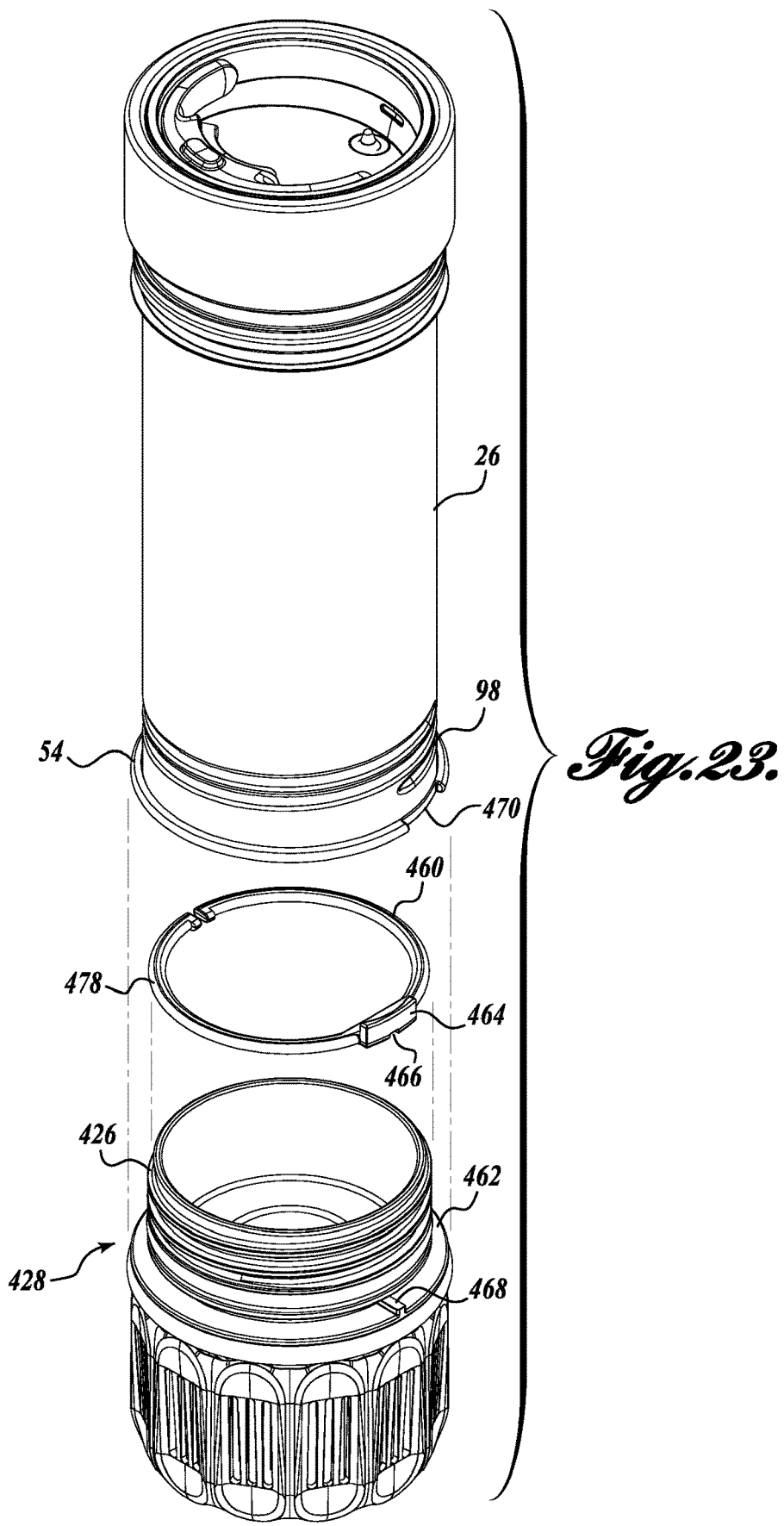

FILTRATION CONTAINER ASSEMBLIES AND METHODS

CROSS-REFERENCES TO RELATED APPLICATIONS

This application is continuation of Ser. No. 13/926,496, filed Jun. 25, 2013, to issue as U.S. Pat. No. 10,710,007, which claims the benefit of U.S. Provisional Application No. 61/664,073, filed Jun. 25, 2012, U.S. Provisional Application No. 61/675,267, filed Jul. 24, 2012, and U.S. Provisional Application No. 61/826,460, filed May 22, 2013, the disclosures of which are hereby incorporated by reference in the present application in their entirety.

BACKGROUND

Some people prefer to filter tap water to remove unwanted impurities, tastes, heavy metals and other toxins. Moreover, when collecting water from a natural, untreated source, such as a lake or a stream, or when traveling in a foreign country that does not treat its tap water, it is important to either filter or treat water for microbial contamination.

Tap water is currently filtered using several different kinds of filtering systems, for example, faucet attachments, refrigerator filter systems, or pitcher or basin-type drip filtration system, from which a user may pour filtered water from the filter systems into his or her cup. Natural, untreated water is typically filtered using a hand-held filter pump that typically uses vacuum pressure to draw water into the filter. Improved filter assemblies using positive pressure are desirable because drip filtering processes can take a long time and vacuum filtering processes can be hard work for the user.

Positive pressure coffee and tea presses having a single container generally include a plunger received in an outer container. The plunger typically includes a screen filter mounted at the end of a shaft. Hot water is mixed with coffee grounds in the container, and the shaft is pressed down by the user into the container. As the shaft is pressed down, the screen filter presses the coffee grounds to the bottom of the container, while allowing the filtered coffee to pass through the screen to the top of the container. Depending on the tightness of the fit of the screen filter in the container, some grounds may pass to the filtered coffee around the outer perimeter of the screen filter, resulting in undesirable coffee grounds in the user's coffee. Because of the likeliness of contamination in the filtered coffee, a "coffee-press" type water filter is not a good design for water filtration.

Therefore, there exists a need for an improved positive-pressure filter assembly that can improve the experience for a user in filtering water, coffee, and other liquids. There also exists a need for other improvements in container assemblies, such as improved lid assemblies.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In accordance with one embodiment of the present disclosure, a filtration container assembly is provided. The assembly generally includes an outer container having a first end and a second end and defining an inner cavity. The assembly further includes a plunging assembly configured to be received within the outer container inner cavity, wherein the plunging assembly includes an inner sleeve having a first end and a second end and an outer wall defining an inner bore, wherein the outer wall is continuous from the first end to the second end, and a filtration assembly coupled to the inner sleeve at the second end.

In accordance with another embodiment of the present disclosure, a filtration container assembly is provided. The assembly generally includes an outer container having a first end and a second end and defining an inner cavity. The assembly further includes a plunging assembly configured to be received within the outer container inner cavity, wherein the plunging assembly includes an inner sleeve having a first end and a second end and defining an inner bore, wherein the cross-sectional area of the inner sleeve is substantially the same at the first end and the second end, and a filtration assembly coupled to the inner sleeve at the second end.

In accordance with another embodiment of the present disclosure, a method of filtering liquids is provided. The method generally includes obtaining an outer container having an inner cavity and filling at least a portion of the outer container with a liquid. The method further includes obtaining a plunging assembly having an inner sleeve having a first end and a second end and defining an inner bore, wherein the plunging assembly is configured to be received within the inner cavity of the outer container, wherein the inner sleeve has a continuous outer wall extending from the first end to the second end, and wherein the plunging assembly includes a filter coupled to the plunging assembly at the second end. The method further includes pressing the plunging assembly into the inner cavity of the outer container, such that the liquid flow from the inner cavity of the outer container through the filter and into the inner sleeve of the plunging assembly.

In accordance with another embodiment of the present disclosure, a filtration container assembly is provided. The assembly generally includes an outer container having a first end and a second end and defining an inner cavity. The assembly further includes a plunging assembly configured to be received within the outer container inner cavity. The assembly further includes a lid assembly configured for attachment to the outer container first end, wherein the lid assembly includes a handle that is positionable for closing a drinking portion of the lid assembly.

In accordance with another embodiment of the present disclosure, a container assembly is provided. The assembly generally includes an outer container having a first end and a second end and defining an inner cavity, and a lid assembly configured for attachment to the outer container first end, wherein the lid assembly includes a handle that is positionable for closing a drinking portion of the lid assembly.

In any of the embodiments described herein, the outer container may have a first open end and a second closed end.

In any of the embodiments described herein, the outer container may have a substantially cylindrical outer wall defining the inner cavity.

In any of the embodiments described herein, the inner sleeve may have a substantially cylindrical outer wall.

In any of the embodiments described herein, the inner cavity of the outer container and the inner sleeve of the plunging assembly may be concentric with one another.

In any of the embodiments described herein, the plunging assembly may be configured to nest in the inner cavity of the outer container.

In any of the embodiments described herein, the filtration assembly may include a filter selected from the group consisting of screens, sieve filters, granular-activated carbon filters, metallic alloy filters, microporous ceramic filters, a carbon block resin filters, electrostatic nanofiber filters, reverse osmosis filters, ion exchange filters, UV light filters, hollow fiber membrane filters, and ultra-filtration membrane filters.

In any of the embodiments described herein, the filtration assembly may include a device for pressure release.

In any of the embodiments described herein, the device for pressure release may include a floating seal.

In any of the embodiments described herein, the floating seal may be received within an annular space along the outer perimeter of the filtration assembly.

In any of the embodiments described herein, the floating seal may include a floating portion and a non-floating portion.

In any of the embodiments described herein, the device for pressure release may include a pressure release valve.

In any of the embodiments described herein, the device for pressure release may be configured to maintain a seal when the plunging assembly is being inserted into the outer container.

In any of the embodiments described herein, the device for pressure release may be configured to release the seal when the plunging assembly is being removed from the outer container.

In any of the embodiments described herein, the plunging assembly may include a collar assembly for interfacing with the outer container.

In any of the embodiments described herein, the collar assembly may be configured to create an interference fit between the plunging assembly and the outer container.

In any of the embodiments described herein, the collar assembly may include a seal and a collar.

In any of the embodiments described herein, the collar assembly may be configured to engage with a plurality of depressions in the outer wall of the inner sleeve.

In any of the embodiments described herein, the filtration assembly may be releasably coupled to the inner sleeve at the second end.

In any of the embodiments described herein, the filtration assembly and the inner sleeve may be releasably coupled by a threaded connection.

In any of the embodiments described herein, the inner sleeve may include threads at the second end.

In any of the embodiments described herein, the filtration assembly may include a housing having threads on the outer perimeter of the housing.

In any of the embodiments described herein, the filtration assembly may include a housing having threads extending from the filtration assembly.

In any of the embodiments described herein, the filtration container assembly may further include a filter lock configured for lockingly engaging the filtration assembly and the inner sleeve.

In any of the embodiments described herein, the filter lock may disengage when a grip portion is pulled away from the outer surface of the outer wall of the inner sleeve.

In any of the embodiments described herein, the filtration container assembly may further include a lid assembly configured for attachment to the first end of the outer container.

In any of the embodiments described herein, the lid assembly may include a plurality of grooves configured for coupling with a plurality of extensions on the inner surface of the inner bore of the inner sleeve.

In any of the embodiments described herein, the lid assembly may be rotatably couplable with the outer container.

In any of the embodiments described herein, the lid assembly may include a handle that is positionable in a first position for closing a drinking portion of the lid assembly.

In any of the embodiments described herein, the lid assembly handle may be positionable in a second position for depressing a valve to allow air entry into the outer container.

In any of the embodiments described herein, the lid assembly may include a planar exterior surface selected from the group consisting of substantially perpendicular to a central axis of the filtration container assembly and tilted relative to substantially perpendicular.

DESCRIPTION OF THE DRAWINGS

The foregoing aspects and many of the attendant advantages of this disclosure will become more readily appreciated as the same become better understood by reference to the following detailed description, when taken in conjunction with the accompanying drawings, wherein:

FIGS. 12A-12D are cross-sectional views of the filtration container assembly of FIG. 1, showing various stages of the filtration process;

FIGS. 13-16B are cross-sectional and exploded views of a filtration assembly in accordance with another embodiment of the present disclosure;

FIGS. 20-27 are various views of a filtration assembly in accordance with yet another embodiment of the present disclosure.

DETAILED DESCRIPTION

Figure 1:
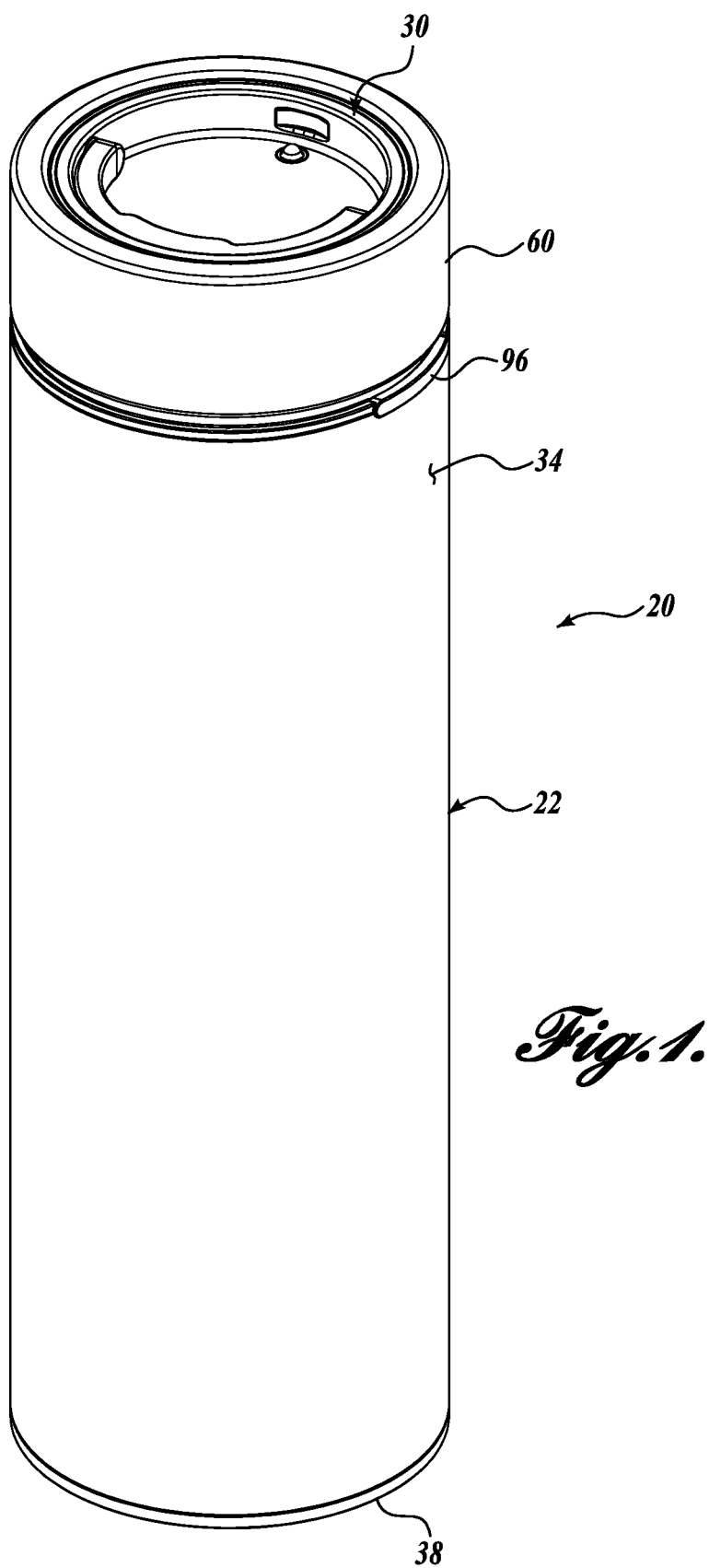
FIG. 1 is an isometric view of a filtration container assembly in accordance with one embodiment of the present disclosure.

The detailed description set forth below in connection with the appended drawings, where like numerals reference like elements, is intended as a description of various embodiments of the disclosed subject matter and is not intended to represent the only embodiments. Each embodiment described in this disclosure is provided merely as an example or illustration and should not be construed as preferred or advantageous over other embodiments. The illustrative examples provided herein are not intended to be exhaustive or to limit the disclosure to the precise forms disclosed. Similarly, any steps described herein may be interchangeable with other steps, or combinations of steps, in order to achieve the same or substantially similar result.

In the following description, numerous specific details are set forth in order to provide a thorough understanding of exemplary embodiments of the present disclosure. It will be apparent to one skilled in the art, however, that many embodiments of the present disclosure may be practiced without some or all of the specific details. In some instances, well-known process steps have not been described in detail in order not to unnecessarily obscure various aspects of the present disclosure. Further, it will be appreciated that embodiments of the present disclosure may employ any combination of features described herein.

Embodiments of the present disclosure are generally directed to filtration and container assemblies and methods. In the illustrated embodiment of FIGS. 1-3, a filtration container assembly 20 generally includes an outer container 22 and a plunging assembly 24, which includes an inner sleeve 26 and a filtration assembly 28. The filtration container assembly 20 may further include a lid assembly 30. As described in greater detail below in accordance with embodiments of the present disclosure, when the outer container 22 is at least partially filled with liquid, the user can exert pressure on the inner sleeve 26 to nest the plunging assembly 24 within the outer container 22, thereby using positive pressure to displace the liquid in the outer container 22 through the filtration assembly 28 into the inner sleeve 26.

Although shown and described as a personal water filtration container assembly, it should be appreciated that other embodiments are within the scope of the present disclosure. For example, an assembly within the scope of the present disclosure may be configured as a large container, such as a jug, cooler, barrel, or tank, or as a smaller container, such as a bottle or sippy cup. It should be appreciated that larger form factors may use a crank or even an electric motor to achieve the positive pressure value required for filtration.

Moreover, coffee or tea presses having an inner sleeve and outer container, but which include screen or sieve filters instead of particulate and microbial filters, are within the scope of the present disclosure. In accordance with embodiments of the present disclosure, suitable filters for use in the container assembly, include, but are not limited to screens, sieve filters, granular-activated carbon filters, metallic alloy filters, microporous ceramic filters, a carbon block resin filters, electrostatic nanofiber filters, reverse osmosis filters, ion exchange filters, UV light filters, hollow fiber membrane filters, and ultra-filtration membrane filters.

Any directional references in the present application, such as "up", "down", "top", "bottom", etc., are intended to describe the embodiments of the present disclosure with reference to the orientations provided in the figures and are not intended to be limiting.

Figure 2:
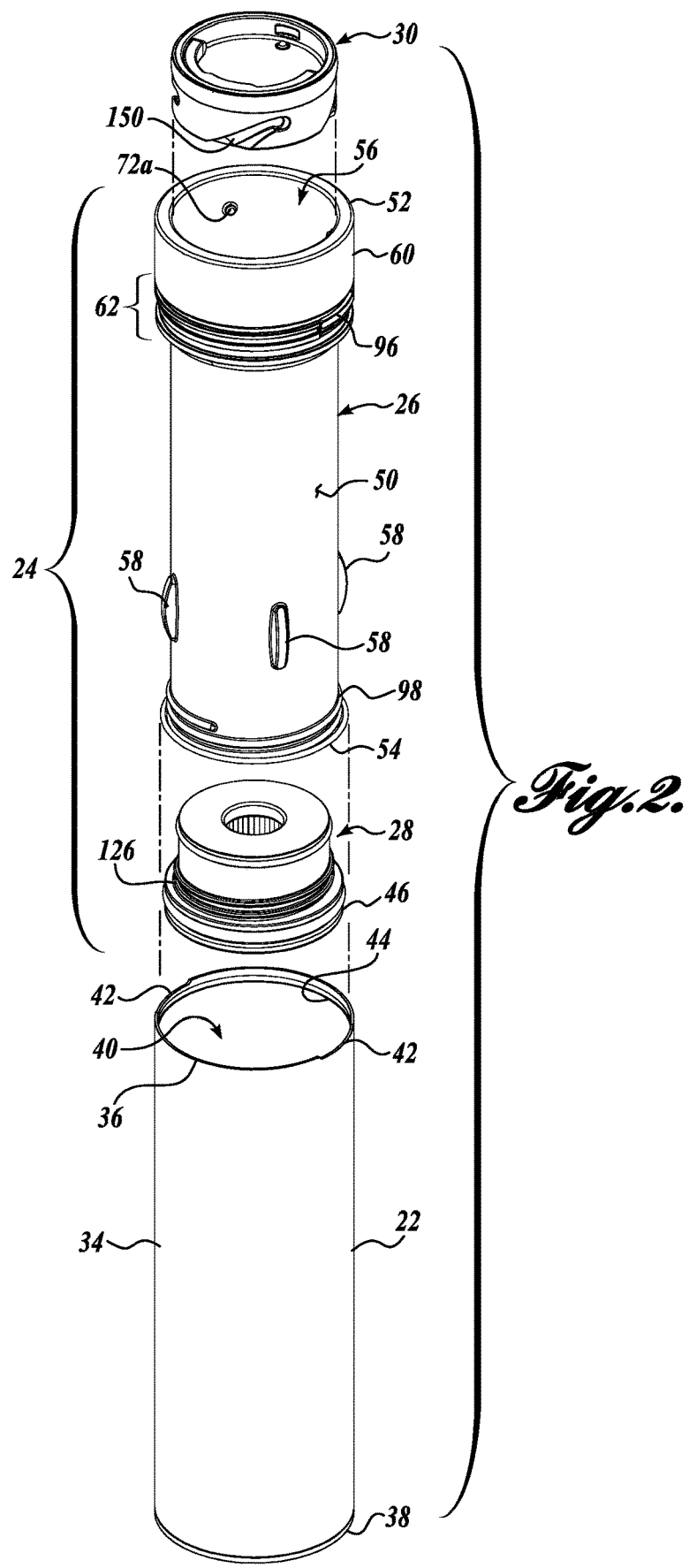
FIG. 2 is an exploded view of the filtration container assembly of FIG. 1.

Referring to FIGS. 1 and 2, the outer container 22 will now be described. In the illustrated embodiment, the outer container 22 is a substantially cylindrical cup having a wall 34 extending between a first open end 36 and a second closed end 38 and defining an inner cavity 40. The term "substantially" is used herein to include standard engineering and/or manufacturing tolerances. Although shown in the illustrated embodiment as having a substantially cylindrical wall 34 on both inner and outer surfaces, it should be appreciated that other cross-sectional shapes are also within the scope of the present disclosure. For example, the outer container 22 may have a substantially cylindrical inner cavity 40, but a non-cylindrical outer surface. As described in greater detail below, a substantially cylindrical inner cavity 40 is designed and configured to mate with one embodiment of the filtration assembly 28 described herein.

At the first end 36, the outer container 22 includes optional notches 42 along the top perimeter of the outer wall 34. Near the first end 36, the outer container 22 further includes an internal annular groove 44 on the inner surface of the wall 34. It should be appreciated that the annular groove 44 may also be positioned on the outer surface of the wall 34. Both the notches 42 and the annular groove 44 are designed and configured for assisting in the interface between the outer container 22 and the plunging assembly 24, as described in greater detail below.

The outer container 22 is configured to receive liquid, for example, unpurified or unfiltered tap or water from a natural, untreated source. In that regard, when in use, the outer container 22 may be filled or at least partially filled with liquid.

Figure 3:
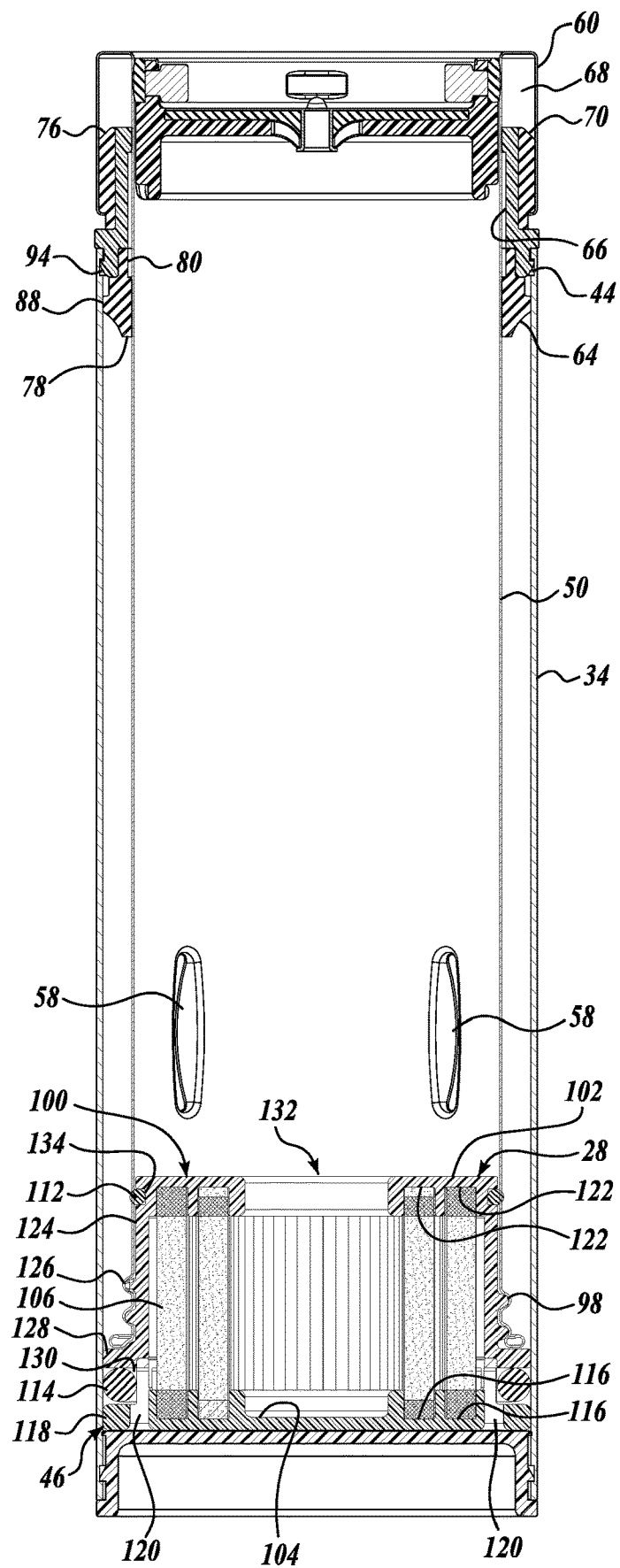
FIG. 3 is a cross-sectional view of the filtration container assembly of FIG. 1.
Figure 4:
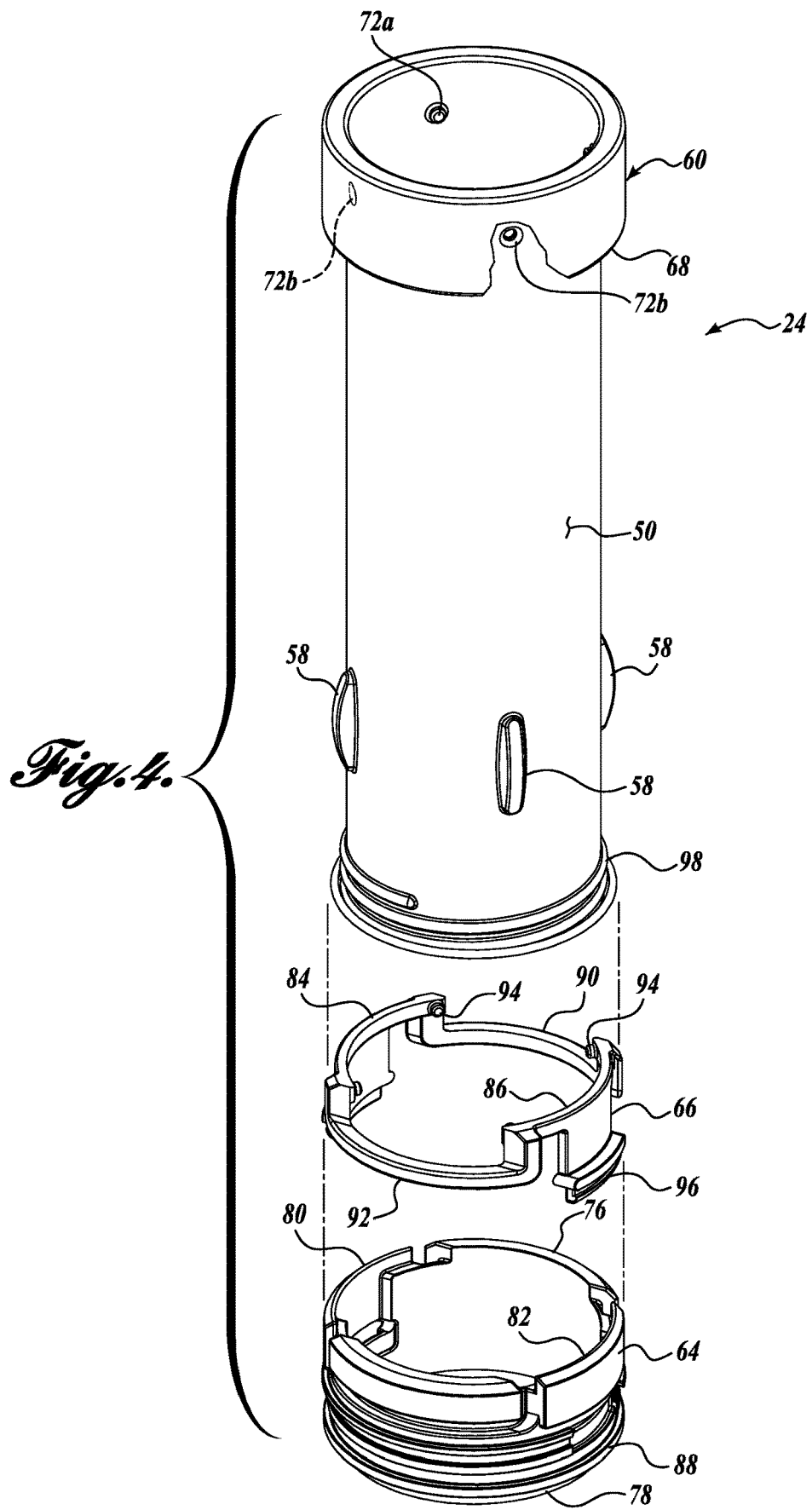
FIG. 4 is an exploded view of the plunging assembly shown in the exploded view of the filtration container assembly of FIG. 2.

Referring to FIGS. 2-4, the plunging assembly 24 will now be described. As mentioned above, the plunging assembly 24 includes the inner sleeve 26 and the filtration assembly 28, both of which are designed to be received within the inner cavity 40 of the outer container 22. In the illustrated embodiment, the inner sleeve 26 has a wall 50 extending between a first open end 52 and a second open end 54 and defining an inner bore 56. Therefore, the inner sleeve 26 has a continuous sidewall to prevent the migration of contaminants into the filtered liquid that is stored in the inner sleeve 26.

The inner sleeve 26 is configured to move like a piston relative to outer container 22, and therefore, is designed to be received within the outer container 22. Although not required, the inner sleeve 26 may have a substantially consistent cross-sectional area and/or shape along the length of inner sleeve 26. Although shown as a substantially cylindrical outer container 22, it should be appreciated that the outer container 22 may be configured to have any cross-sectional shape, so long as the inner cavity 40 of the outer container 22 and the outer wall 50 of the inner sleeve 26 are capable of nesting together. In one embodiment of the present disclosure, the inner sleeve 26 when nested is wholly contained within the inner cavity 40 of the outer container 22. In the illustrated embodiment, the inner cavity 40 of the outer container 22 is substantially cylindrical, and the plunging end 46 of the plunging assembly 24 is configured to form a seal with inner cavity 40 through the piston movement of the plunging assembly 24 (compare FIGS. 12A, 12B, and 12C).

As described in greater detail below, the inner sleeve 26 includes various features for interfacing with other parts of the filtration container assembly 20. For example, optional guides 58 positioned on the outer surface of wall 50 of the inner sleeve 26 allow for a guided, but spaced fit between the inner sleeve 26 and the outer container 22. Alternatively, a spacer, for example, made of plastic silicon, or rubber, which may be a seal, gasket, roller, or any other suitable spacer, may be used in place of guides 58. A plurality of depressions 72b on the outer surface of wall 50 near the first end 52 of the inner sleeve 26 (see FIG. 4) allow for a secure fit between the body of the inner sleeve 26 and the collar assembly 62, as described in greater detail below. Moreover, on the inner surface of the inner bore 56, the inner sleeve 26 includes a plurality of extensions 72a for interfacing with the lid assembly 30 (see FIGS. 2 and 4).

At the first open end 52, the inner sleeve 26 is designed and configured to interface with the first open end 36 of the outer container In that regard, the inner sleeve 26 may include an annular rim 60 and a collar assembly 62 for interfacing with the first open end 36 of the outer container 22. When the inner sleeve 26 and the outer container 22 are coupled together, the collar assembly 62 assists in maintaining the coupling between the inner sleeve 26 and the outer container 22 and prevents decoupling. In the illustrated embodiment, this coupling is maintained by interference fit; however, it should be appreciated that threaded attachment and other coupling attachments besides interference fit are also within the scope of the present disclosure.

As can be seen in FIGS. 3 and 4, the annular rim 60 hangs over the wall 50 of the inner sleeve 26, creating a space 68 beneath the rim 60. In the illustrated embodiment, collar assembly 62 includes a seal 64 and a collar 66 that are configured to nest with one another inside at least a portion of the space 68 and extend from the space 68 adjacent the annular rim 60. In that regard, the seal 64 may be made from a flexible material capable of compression, such as silicon or rubber. The collar 66 may be more rigid, for example, manufactured as an injected molded plastic part. The jogged shape of the collar 66, as described in greater detail below, allows for ease of assembly with the seal 64.

In the illustrated embodiment, the seal 64 includes an annular body having a first end 76 and a second end 78. At the first end 76, the seal 64 includes first and second interface areas 80 and 82 for receiving and mating with first and second locking portions 84 and 86 of the collar 66. Moreover, the first end 76 of the seal 64 is configured to be received within the space 68 beneath the annular rim 62. At the second end 78, the seal 64 includes a seal ridge 88 configured to be received within the outer container 22 and to form a seal therewith. It should be appreciated, however, that the outer container 22 and the inner sleeve 26 may be mated together without a locking mechanism, for example, using a plug seal fit (for example, similar to a wine cork fit), a magnetic attachment, a latch, or any other suitable mating mechanism.

As mentioned above, the collar 66 includes first and second locking portions 84 and 86. These locking portions 84 and 86 are coupled to connecting portions 90 and 92 to form a collar structure. To maintain positioning relative to the inner sleeve 26, the collar 66 includes a plurality of inner extensions 94 that are configured to engage with the plurality of depressions 72b in the outer wall 50 of the inner sleeve 26 (see FIG. 4). (Of note, in the illustrated embodiment, the plurality of depressions 72b are formed by punching the plurality of extensions 72a into the wall 50 of the inner sleeve 26.) The locking portions 84 and 86 each include a respective tab 96 that is configured to mate with each of the notches 42 in the first ends 36 of the outer container 22 (see FIGS. 1 and 2).

Referring now to FIGS. 2 and 3, at the second open end 54 of the inner sleeve 26, the inner sleeve 26 is configured to couple with the filtration assembly 28. In the illustrated embodiment, the second open end 54 of the inner sleeve 26 includes threads 98 for a screw fit interface with opposite threads 126 on the outer perimeter of the filtration assembly 28 (see FIG. 2). Although shown as a screw fit interface between the second open end 54 of the inner sleeve and the filtration assembly 28, it should be appreciated that other interfaces, such as an interference fit interface, are also within the scope of the present disclosure.

Figure 5:
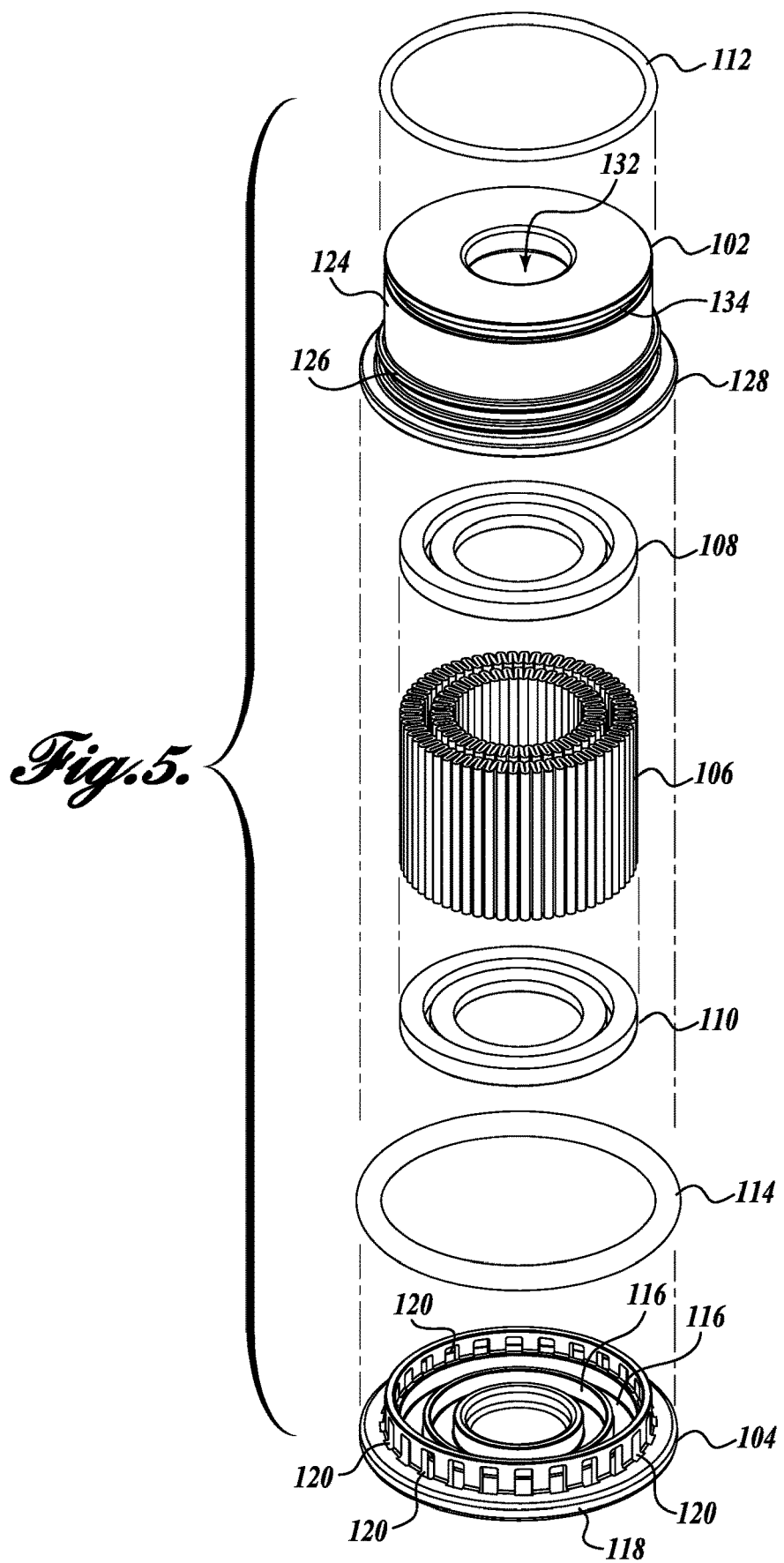
FIG. 5 is an exploded view of the filtration assembly shown in the exploded view of the filtration container assembly of FIG. 2.
Figure 6:
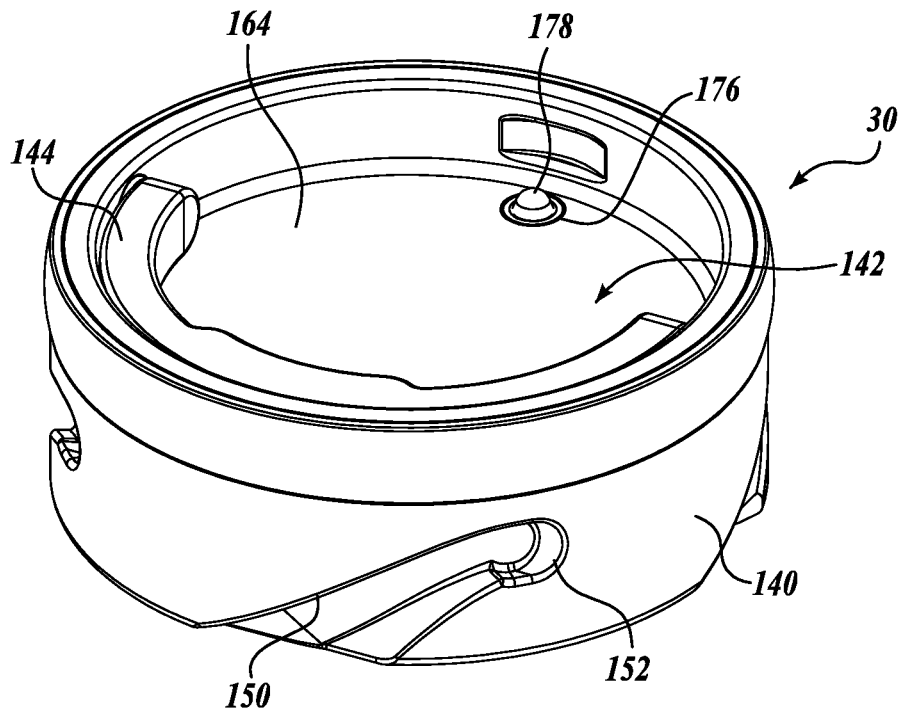
FIGS. 6-11 are various views of the lid assembly shown in the exploded view of the filtration container assembly of FIG. 2.
Figure 7:
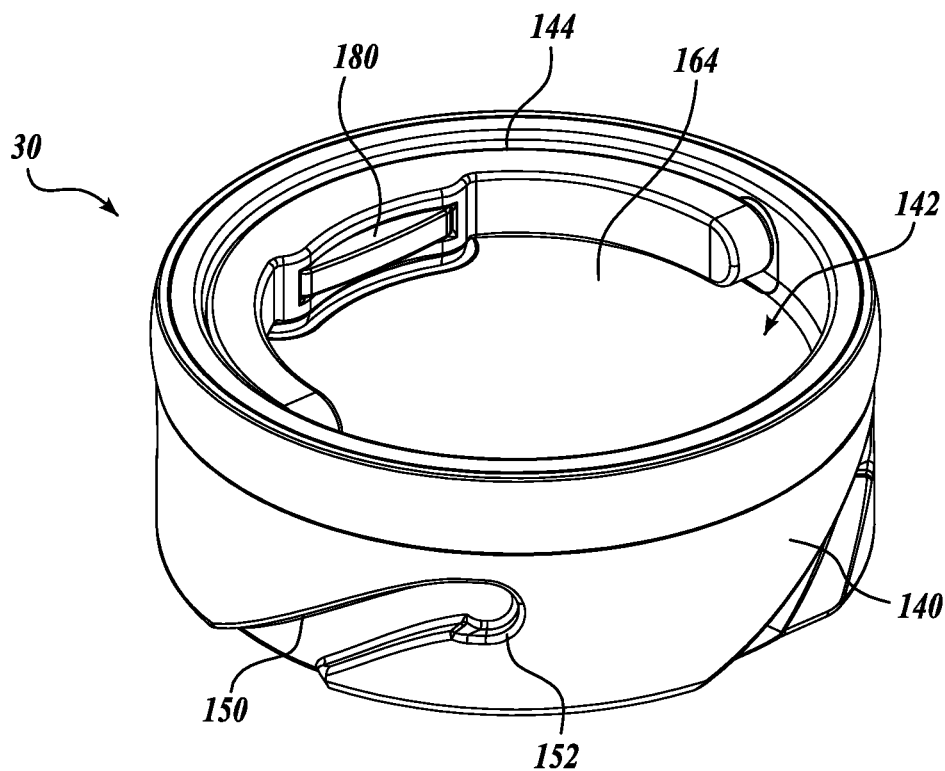

Referring to FIGS. 3 and 5, the filtration assembly 28 will now be described in greater detail. The filtration assembly 28 includes a filter housing 100, filter media 106, and first and second seals 112 and 114 for interfacing with the inner sleeve 26 and outer container 22, respectively. It should be appreciated that the filtration assembly 28 may be removable and replaceable for a new or different filter.

In the illustrated embodiment, the filter housing 100 includes first and second mating portions 102 and 104. First and second mating portions may help simplify assembly processes; however it should be appreciated that the filter housing may also be manufactured as a single piece or to break down into other mating portions.

In the illustrated embodiment, the first mating portion 102 is a cover portion and the second mating portion 104 is a base portion. As can be seen in FIGS. 3 and 5, it can be seen that the base portion 104 includes a plurality of concentric grooves 116 to provide structure to contain the filter media 106, but also to allow the flow of water through the housing 100. Moreover, the base portion 104 includes a base outer rim 118 that is sized and configured to be received within the inner wall 34 of the outer container 22. Along the outer rim 118, the base portion 104 includes a plurality of holes 120 that allow liquid to travel from the outer container 22 into the filtration assembly 28, through the filter media 106, and into the inner sleeve 26, when the filtration assembly 28 is subjected to positive pressure.

Likewise, the cover portion 102 also includes a plurality of concentric grooves 122 to provide structure to contain the filter media 106, but also allow the flow of water through the housing 100. As can be seen in the illustrated embodiment of FIG. 3, the cover portion 102 includes an outer wall 124 having threads 126 for interfacing with threads 98 on the second end 54 of the inner sleeve 26. Moreover, like the base portion 104, the cover portion 102 also includes a base outer rim 128 that is sized and configured to be received within the inner wall 34 of the outer container 22. Center hole 132 in the cover portion 102, allows liquid to pass from holes 120 in the base portion 104 through the filter media 106 into the inner sleeve 26.

Groove 134 on cover portion 102 is configured to receive first seal 112 to form a seal with the inner wall 34 of the inner sleeve 26 when the filtration assembly 28 is coupled to the inner sleeve 26. In the illustrated embodiment, first seal 112 is an o-ring type seal; however, other types of seals are also within the scope of the present disclosure.

Figure 21:
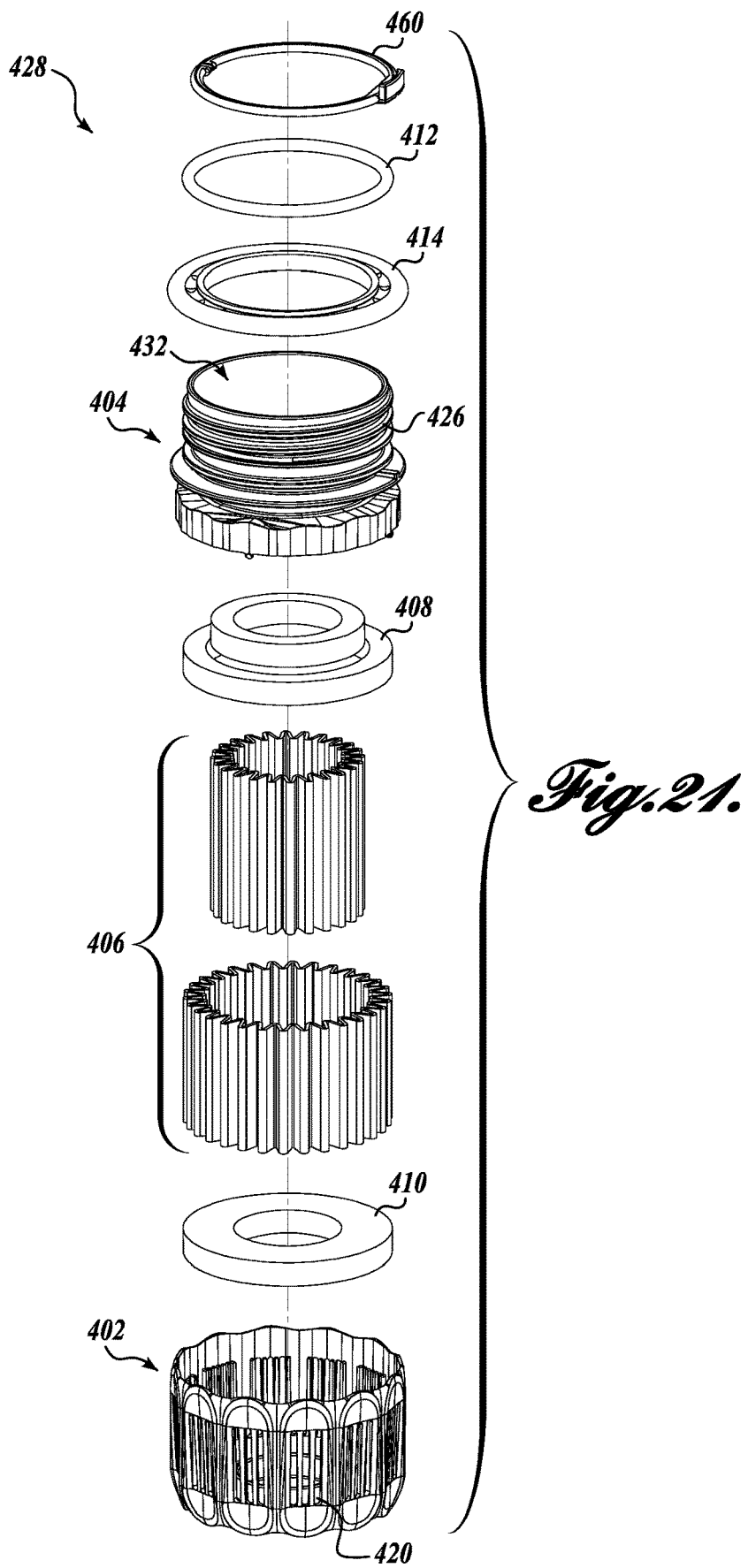

When the cover portion 102 is mated with the base portion 104, spacing, such as a gap 130 between the respective base outer rims 118 and 128 along the outer edge of the housing assembly 100, is provided for receiving second seal 114. It should also be appreciated that the second seal 114 may be received in a groove formed along the outer perimeter of the housing assembly 100. Because the gap 130 is sized to be slightly larger than the diameter of the second seal 114, the second seal 114 may be a "floating" seal that is movable between first "up" and second "down" positions (compare FIGS. 12C and 12D), as will be described in greater detail below. In the illustrated embodiment, second seal 114 is an o-ring type seal; however, other types of seals are also within the scope of the present disclosure. For example, see the floating seal 414 of FIGS. 21-22B.

Contained within the housing is the filter media 106 and first and second filter potting portions 108 and 110. The potting portions 108 and 110 are used to secure and seal the filter media 106 in place. In that regard, the potting portions 108 and 110 may be a liquid or paste potting that is poured or applied into the wells or concentric grooves 116 and 122 in the respective base portion 104 and cover portion 102 of the filter housing 100. In another embodiment, the potting portions 108 and 110 may be formed by ultrasonic welding or other non-liquid, non-paste techniques.

The filtration assembly 28 can therefore be formed by depositing potting in either of the concentric grooves 116 and 122 of respective base and cover portions 104 and 102, placing the filter media 106 in the grooves, allowing the potting to secure the filter media 106 to the housing portion, then flipping the filter media 106 over to apply potting to the other of the concentric grooves 116 and 122 of respective base and cover portions 104 and 102 and allowing the potting to secure the filter media 106 to the housing portion 104 or 102. The purpose of the potting is to seal the filter media 106 within the housing base and cover portions 104 and 102, to prevent seeping of contaminated water and to maintain the filtration assembly 28 as an assembly.

In one embodiment of the present disclosure, the filter media 106 may be a non-woven media filter, for example, including carbon, alumina fibers, silver or any other bacteria, virus, odor or flavor reducing material. The filter media 106 may be capable of filtering, although not limited to, Cryptosporidium, Giardia, viruses, odors, and flavors from liquids. In the illustrated embodiment, the filter media 106 is a double, concentric filter. However, it should be appreciated that single filters are also within the scope of the present disclosure (see FIGS. 14 and 15). Likewise, it should be appreciated that triple and other multiple filters, as well as other types of filters, including but not limited to activated carbon block, reverse osmosis, granular activated carbon, ion exchange, and others, are also within the scope of the present disclosure.

Figure 17:
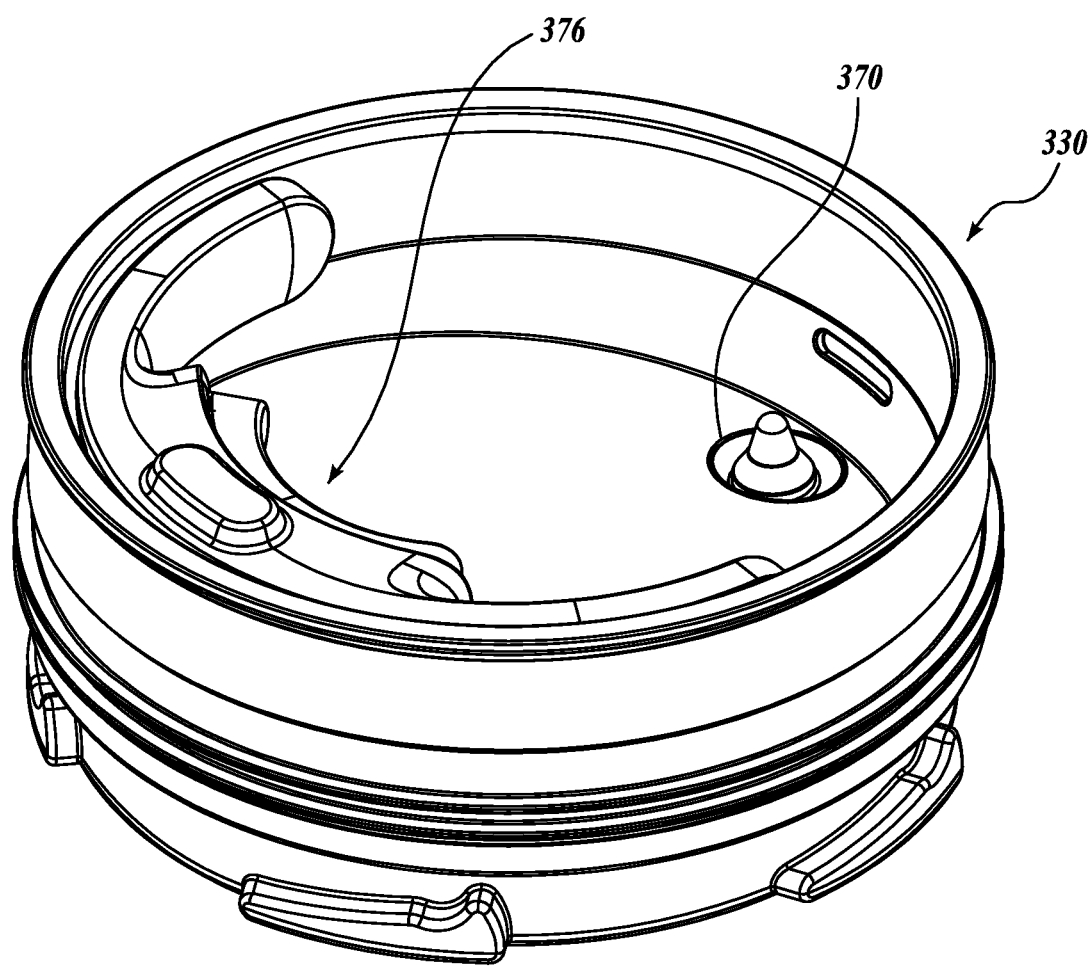
FIGS. 17-19 are various views of a lid assembly in accordance with another embodiment of the present disclosure.
Figure 18:
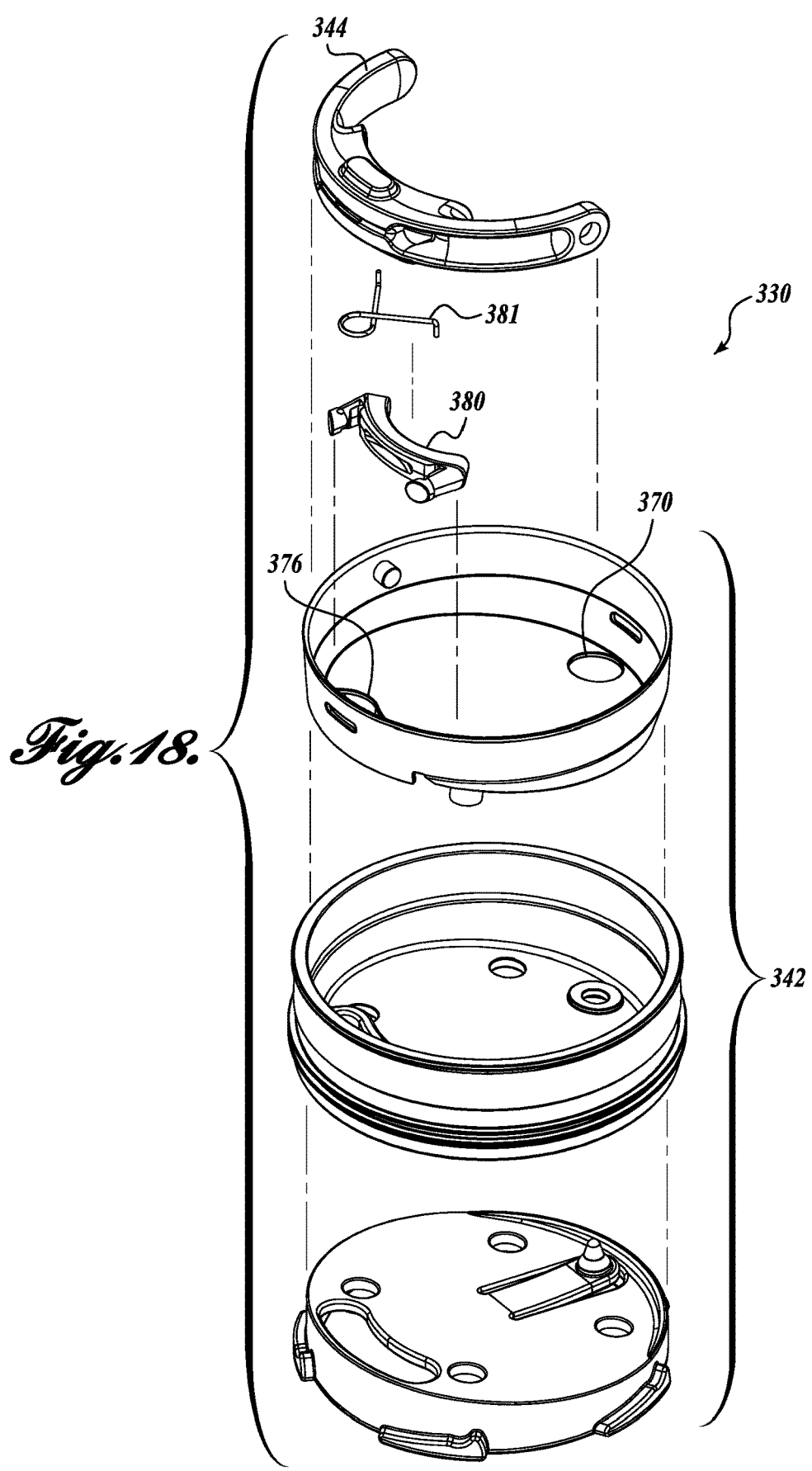
Figure 19:
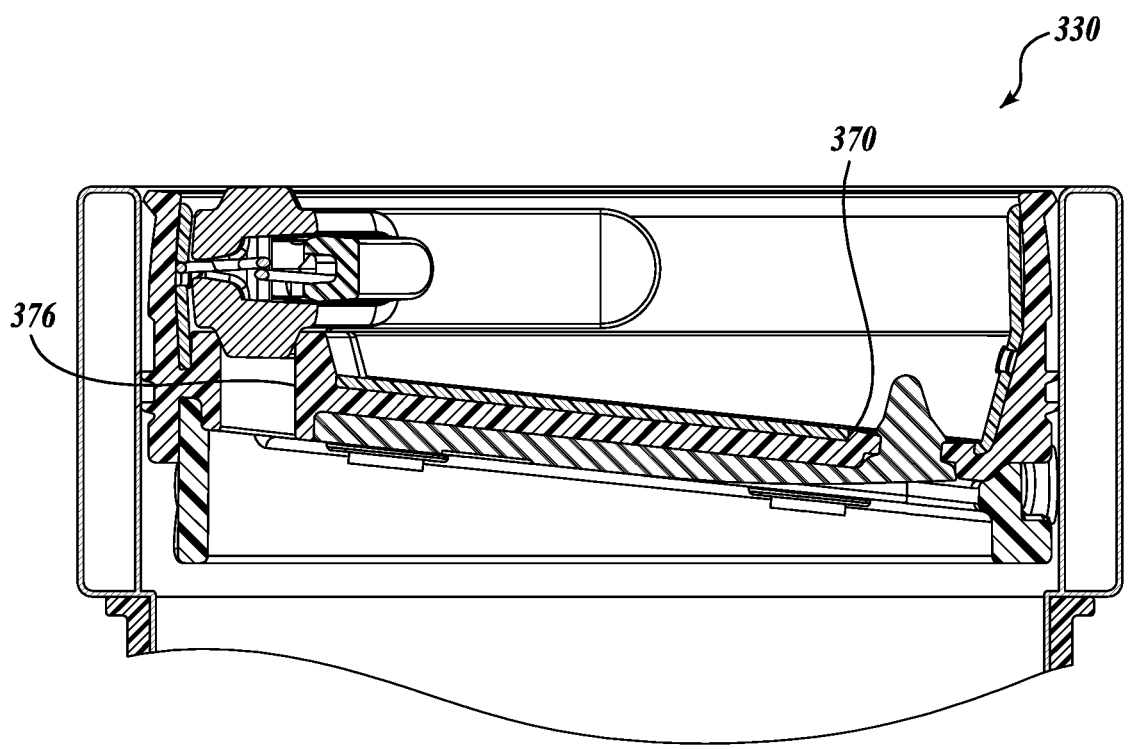
Figure 20:
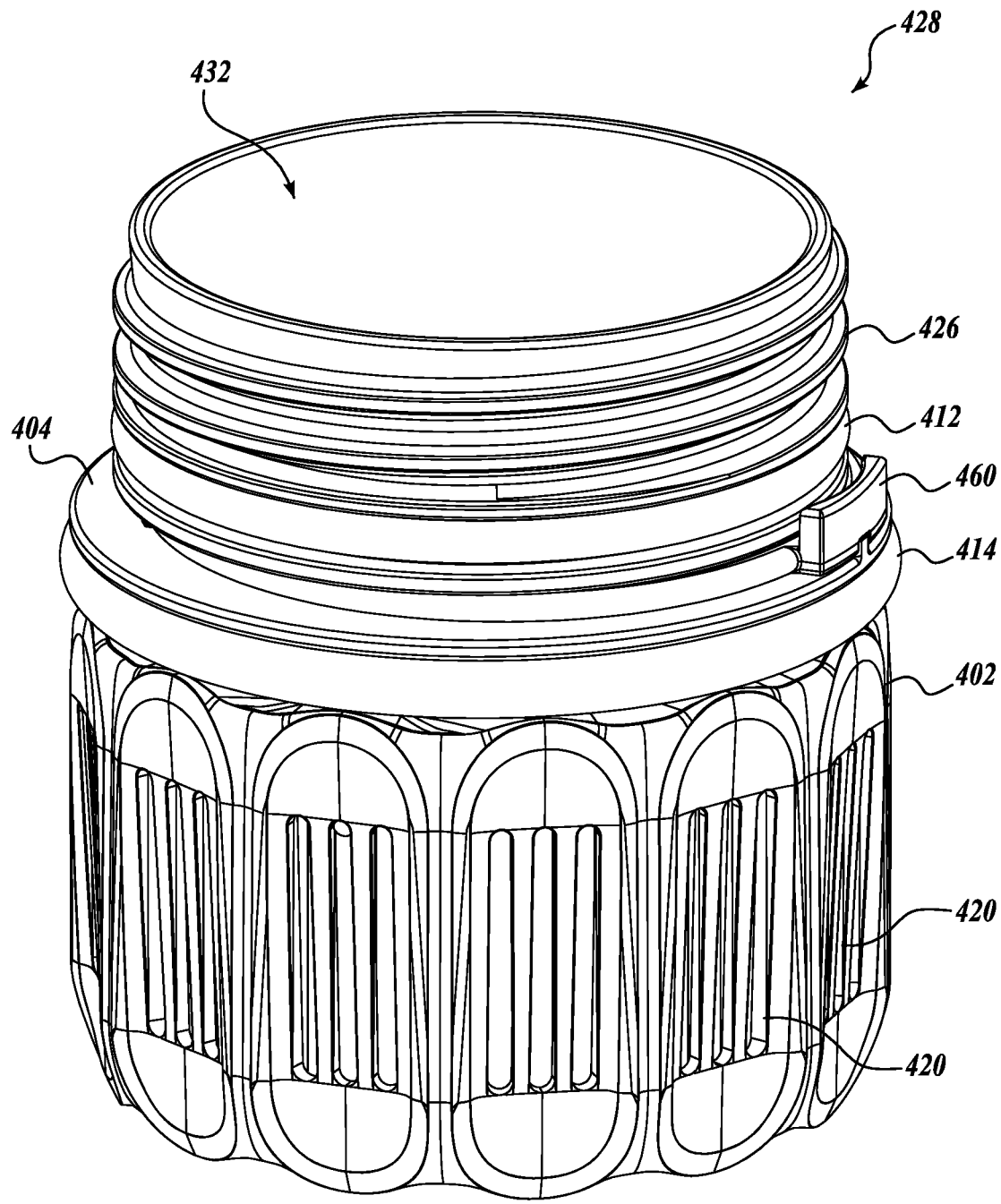

Now referring to FIGS. 6-11, the lid assembly will now be described in greater detail. The lid assembly 30 generally includes an attachment portion 140 for attaching to the annular rim 60 of the inner sleeve 26, a drinking portion 142 for allowing a user to drink liquids from the filtration container assembly 20, and a handle assembly 144. An alternate embodiment is shown in FIGS. 17-19.

The attachment portion 140 includes a plurality of angled grooves 150 for receiving the plurality of extensions 72*a* that extend from the inner surface of the inner bore 56 of the inner sleeve 26 (see, e.g., FIG. 2). At the end of each of the angled grooves 150, a seat 152 in the groove 150 allows the extension 72*a* to seat in place. The extension 72*a* can be removed from the seat by pressing downward on the lid assembly 30 before rotating the extensions 72*a* backward in the grooves 150 to decouple the extensions 72*a* from the grooves 150.

Figure 8:
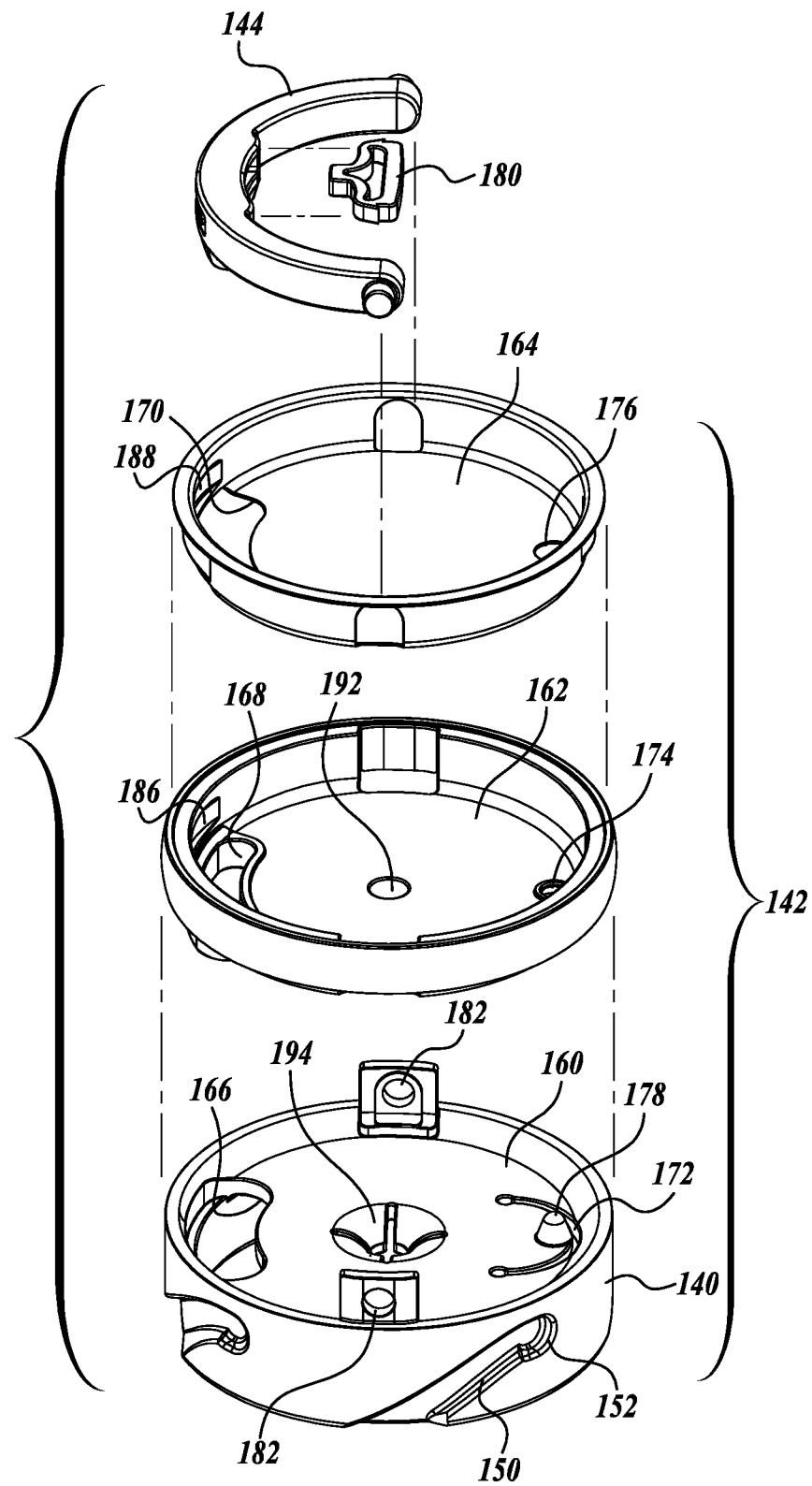
Figure 9:
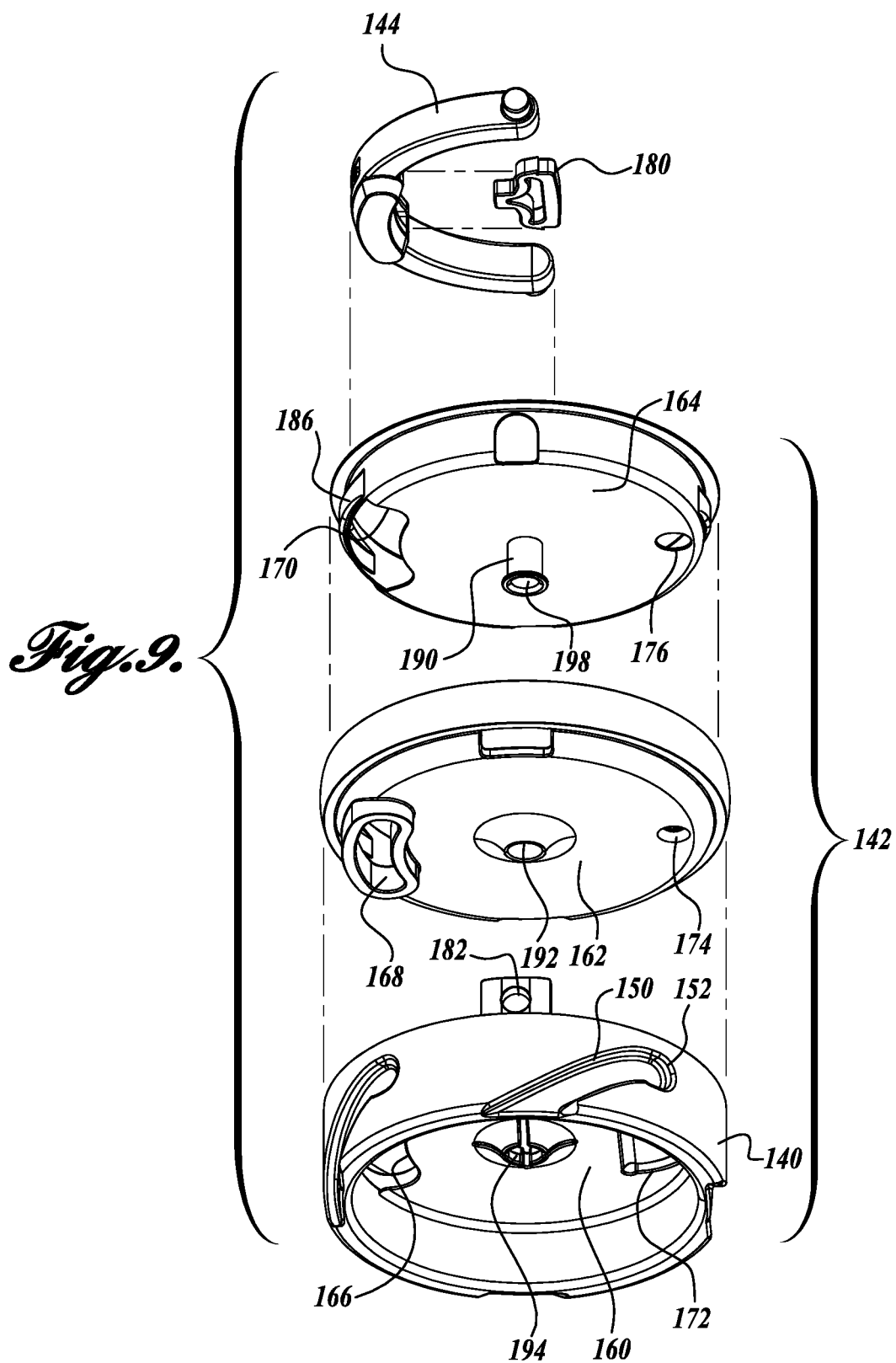
Figure 10:
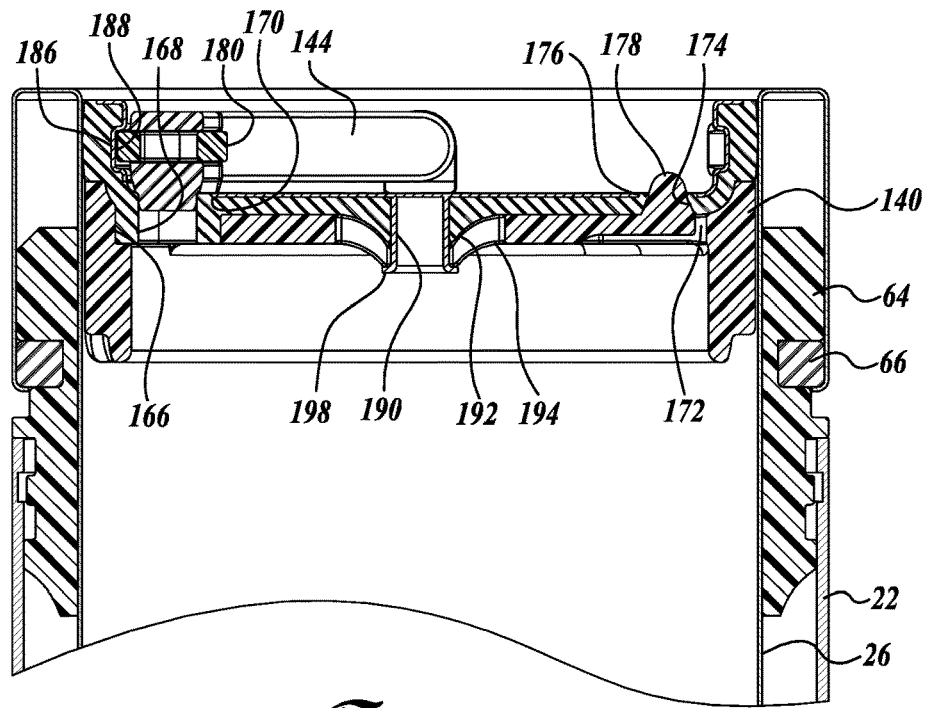
Figure 11:
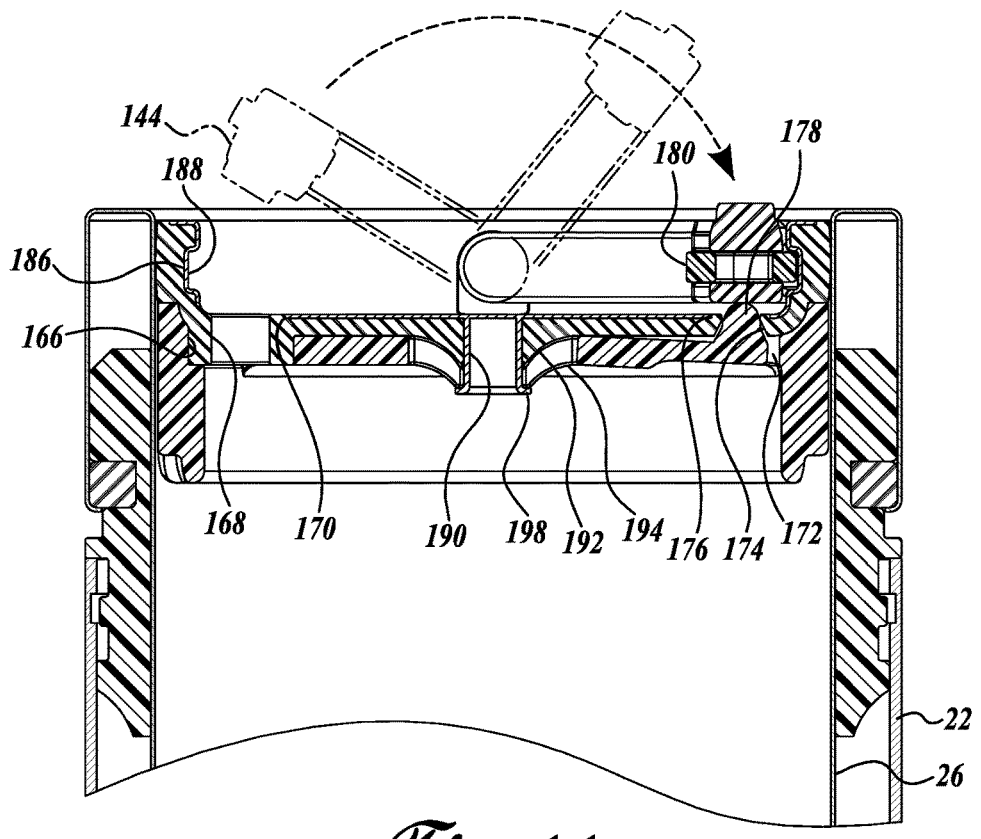

Referring to FIGS. 8 and 9, the drinking portion 142 of the lid assembly 30 includes a first portion 160, a second portion 162, and a third portion 164. In one embodiment of the present disclosure, the first portion 160 is an interface portion for interfacing with the inner sleeve 26. In that regard, the first portion 160 may be made from plastic or another suitable material having flexibility and compressibility properties, In that regard, a plastic first portion 160 helps to eliminate rattling between the lid assembly 30 and the inner sleeve 26. Also, a plastic first portion 160 includes a flexible cantilever valve 178, as descried in greater detail below. The third portion 164 is a finished portion, for example, made from stainless steel, coated metal, plastic, or another suitable material having suitable aesthetic properties. The second portion 162 is a sealing portion, for example, made from silicon or another material having suitable sealing properties. The second portion 162 may provide a seal around the outer perimeter of the lid assembly 30 to act as a gasket between the lid assembly 30 and the inner sleeve 26, as well as around the drinking and air holes 166 and 176 in the first and third portion 160 and 164 (see FIGS. 10 and 11), as described in greater detail below.

Each of the first, second, and third portions 160, 162, and 164 include a respective drinking hole 166, 168, or 170 from which the user receives liquid. On the opposite side of the lid assembly 30, each of the base 160, insert 162, and cover 164 include a respective air hole 172, 174, or 176 from which air enters the inner sleeve 26 to deliver liquid to the user through the drinking hole. The air hole 172 in the base 160 includes a valve 178 that requires depression to allow air entry (see FIG. 11).

The handle assembly 144 couples to handle engagement holes 182 extending from the drinking portion 142 of the lid assembly 30. The handle assembly 144 is movable between a first position covering the drinking hole 166 (see FIG. 10), and a second position depressing the valve 178 (see FIG. 11). When in either of the first or second position, the handle assembly 144 may lock into place, requiring depression of lock release 180. When depressed, the lock release 180 provides a lever action to release the handle assembly 144 from locking engagement with detents 186 and 188 in the second and third portions 162 and 164. When in the upright position, the handle assembly 144 can also be used to twist the lid assembly 30 to rotate grooves 150 past extensions 72*a* and release the engagement of the lid assembly 30.

Referring to FIG. 9, the first, second, and third portions 160, 162, and 164 are mated together during the assembly process by an attachment assembly including a nub 190 extending from the underside of the third portion 164 that is received within receiving portions 192 and 194 on the respective second and first portions 162 and 160. Receiving portion 194 includes a plurality of flexible fingers that form a snap fit with the rim 198 on the end of the nub 190.

Figure 12A:
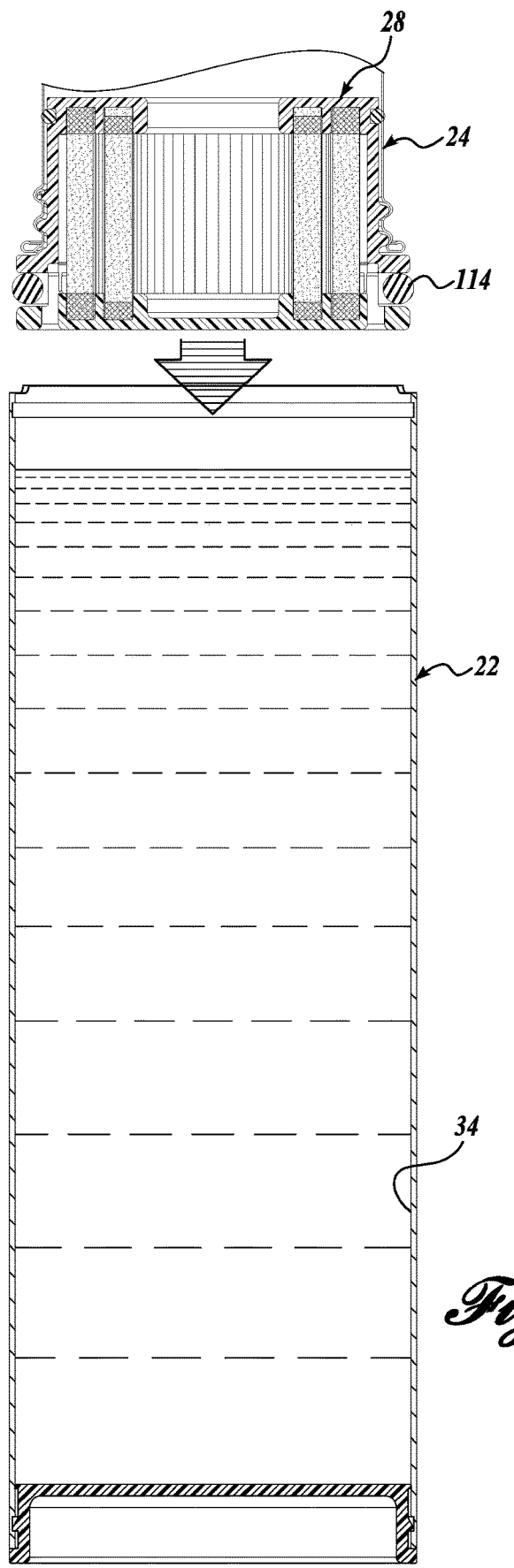

Use of the filtration container assembly 20 will now be described in greater detail with reference to FIGS. 12A-12D. Referring to FIGS. 3 and 12D, the outer container 22 and the plunging assembly 24 are capable of nesting with one another. In that regard, the filter assembly 28 of the plunging assembly 24 seats at the bottom of the inner cavity 40 of the outer container 22, with second seal 114 forming a seal with the inner wall 34 of the outer container 22. Guides 58 extending from the outer wall 50 of the inner sleeve 26 provide suitable spacing between the inner sleeve 26 and the outer container 22. The collar assembly 62 allows the outer container 22 and the plunging assembly 24 to engage with one another and form a seal therebetween.

Figure 12B:
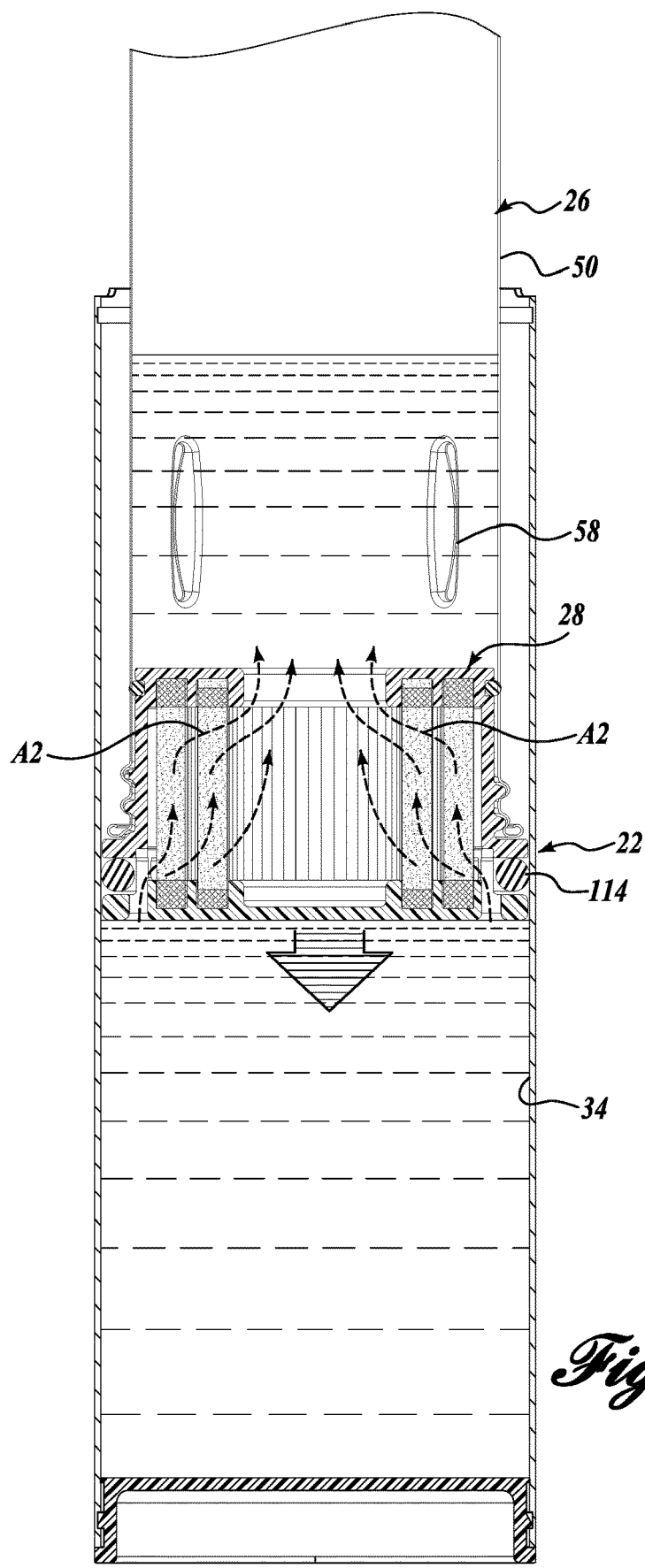
Figure 12C:
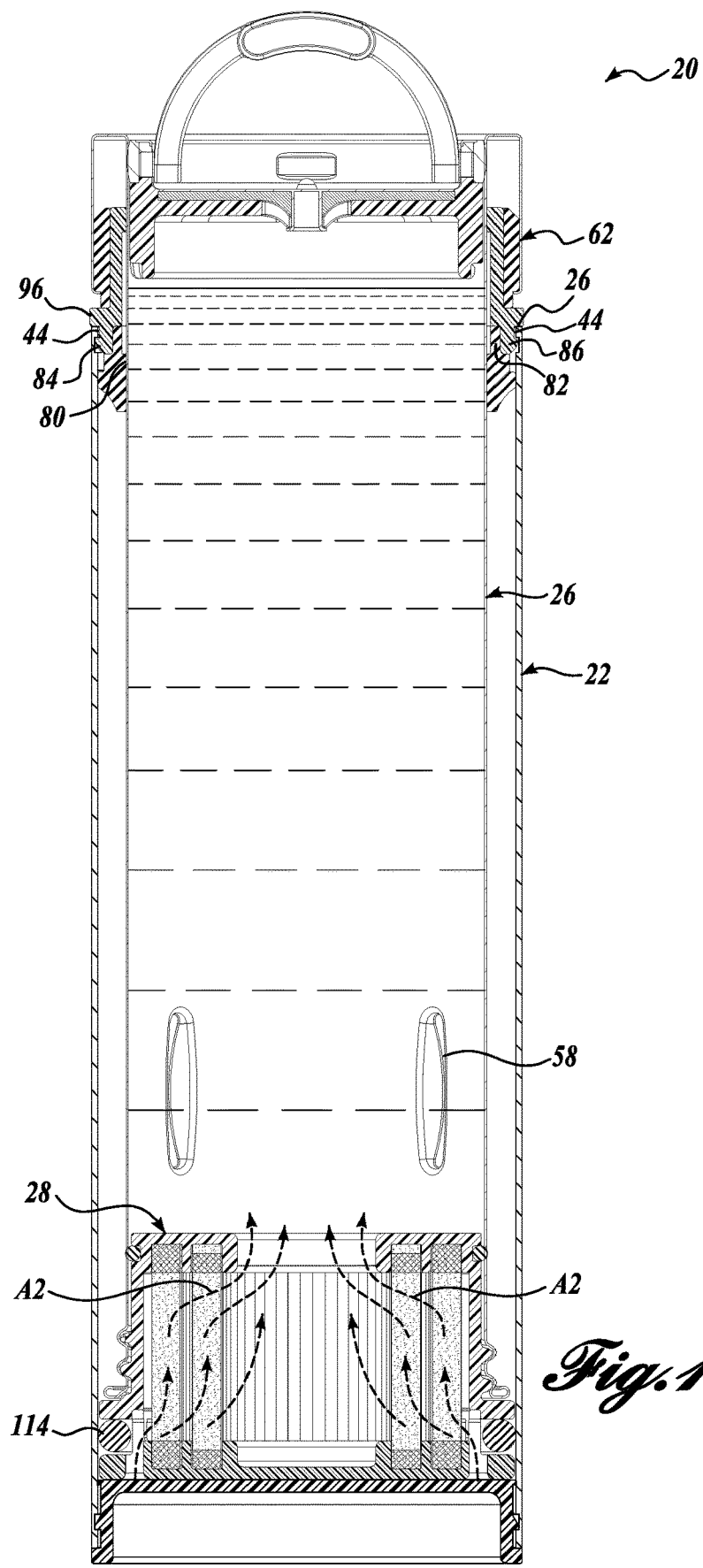

Referring to FIG. 12A, when the plunging assembly 24 has been removed from the outer container 22, the outer container 22 can be filled with liquid. Referring to FIGS. 12B and 12C, as the plunging assembly 24 is inserted into the outer container 22, it filters water from the outer container 22 through the filtration assembly 28 and stores it in the inner sleeve 26.

Referring to FIGS. 12C and 12D, the water has been removed from the inner sleeve 26, and the plunging assembly 24 may be removed from the outer container 22 so that the outer container 22 can be refilled. To release the plunging assembly 24 from the outer container, the user simultaneously grasps the outer container 24 with one hand and presses release tabs 96 with a thumb and either forefinger or index finger on the other hand. When the release tabs 96 are depressed, the first and second locking collar portions 84 and 86 are pressed against the first and second interface sections of the seal 80 and 82 releasing the spring force against the first and second locking collar portions 84 and 86. Therefore, the hook portions of the first and second locking collar portions 84 and 86 are able to disengage from the internal annular groove 44 of the outer container 22, releasing the coupling of the plunging assembly 24 and the outer container 22.

As the plunging assembly 24 is released from the outer container 22, second seal 114 of the filtration assembly 28 moves to the "down" position, creating a pathway for air or liquid to release the pressure in the outer container 22, as shown by the arrows A1.

Referring now to FIG. 12A, with the plunging assembly 24 removed from the outer container 22, the outer container 22 can be filled with liquid. Referring now to FIG. 12B, after the outer container 22 has been filled with liquid, the plunging assembly 24 can be reinserted into the outer container 22 to filter the liquid and store it in the inner bore 56 of the inner sleeve 26. As can be seen in FIG. 12B, when filtering, the second seal 114 of the filtration assembly 28 moves to the "up" position, creating a seal between the outer container 22 and the inner sleeve 26 and thereby forcing all water in the outer container 22 through the filtration assembly 28 and into the inner bore 56 of the inner sleeve 26, as shown by the arrows A2.

Referring to FIG. 12C, when the plunging assembly 24 is fully inserted in the outer container 22, the plunging assembly can be secured in place by securing the hook portions of the first and second locking collar portions 84 and 86 of the collar assembly 62 with the groove 44 in the inner wall 34 of the outer container 22.

Although shown and described as a floating seal for pressure release, it should be appreciated that other methods of pressure release are also within the scope of the present disclosure. Referring now to FIGS. 13-16B, an alternate embodiment of a filtration assembly will be described. The filtration assembly 228 of FIGS. 13-16B is substantially similar to the filtration assembly 28 of FIGS. 1-5 and 12A and 12D, except for differences regarding the pressure release mechanism and the coupling between the first and second housing portions. Like numerals are used for the filtration assembly 228 of FIGS. 13-16B as used for the filtration assembly 28 of FIGS. 1-5 and 12A and 12D, but in the 200 series.

Referring to FIGS. 13-16B, the filtration assembly 228 includes first and second seals 212 and 214 for sealing, respectively, with the inner bore of the inner sleeve (not shown) and the inner cavity of the outer container (not shown). However, in the filtration assembly 228, the second seal 214 is not a floating seal; rather, it is a stationary seal fixedly positioned between the first and second housing portions 202 and 204. Instead of a floating seal pressure release mechanism, the filtration assembly 228 of the illustrated embodiment includes a pressure release valve 260.

Figure 13:
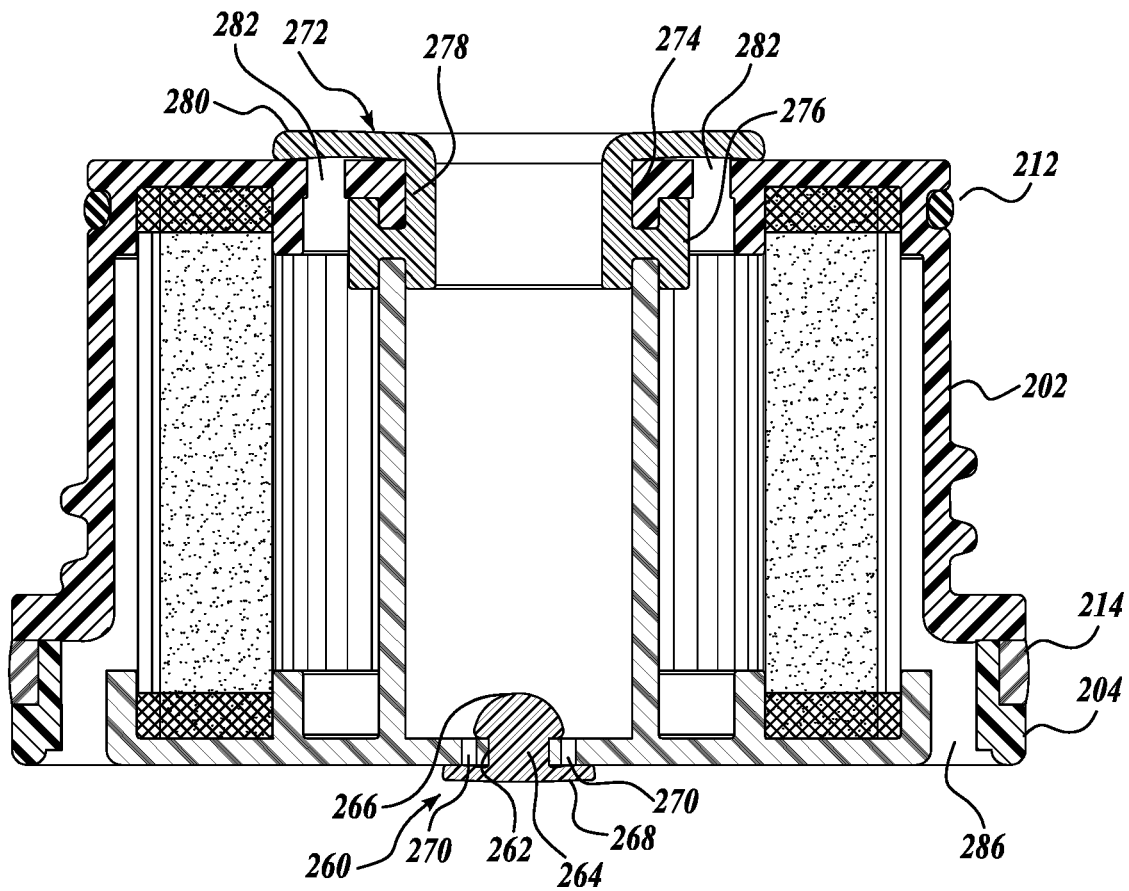
Figure 16A:
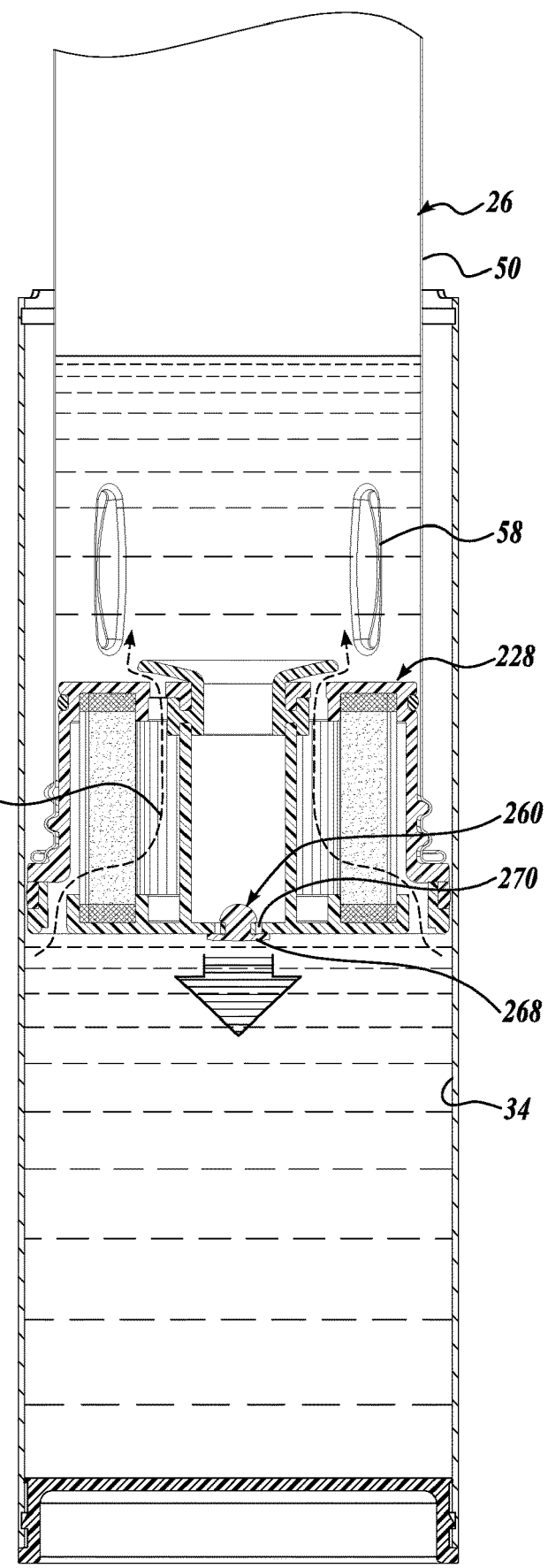
Figure 16B:
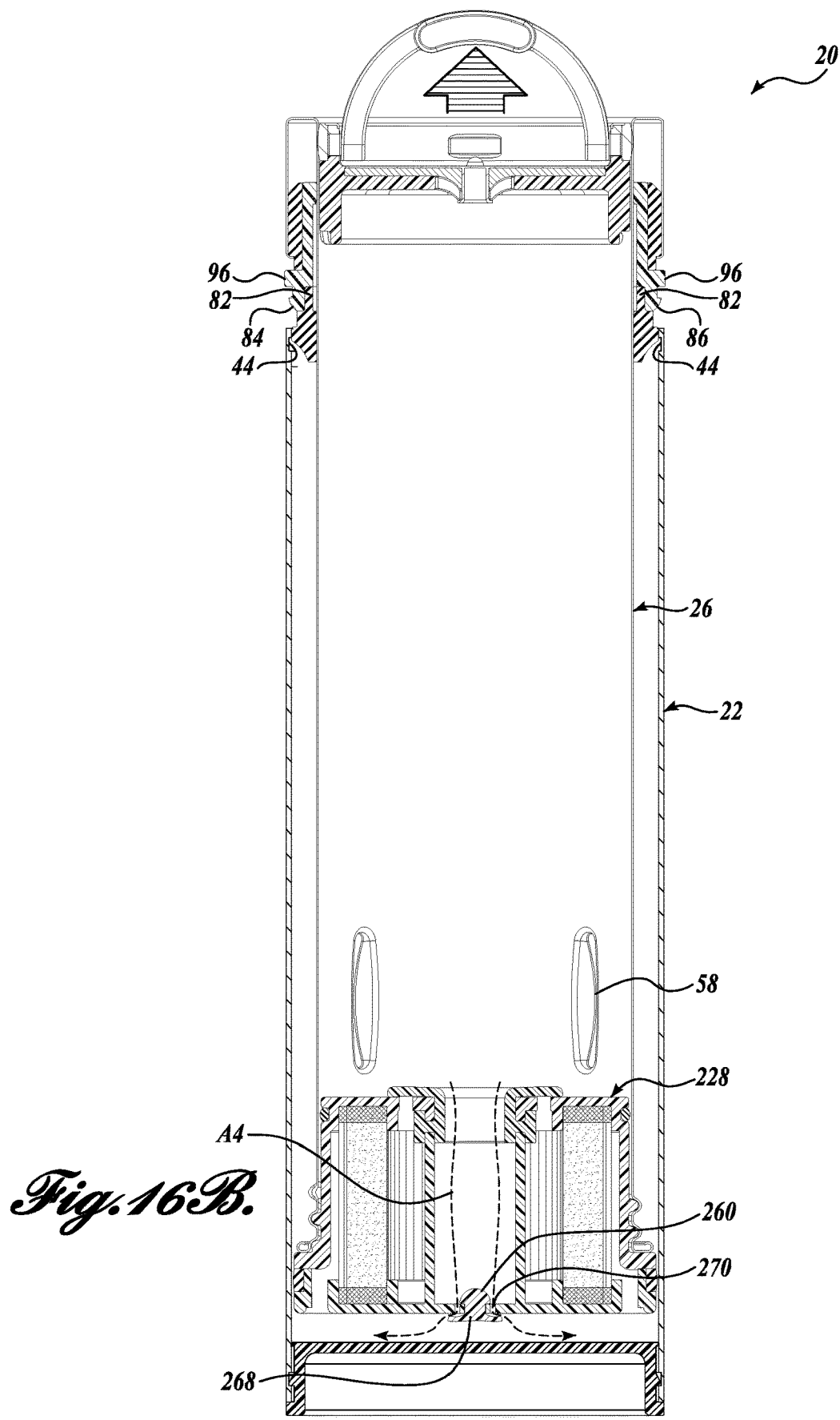

Referring to FIGS. 13 and 15, the pressure release valve 260 couples to hole 262 in the second housing portion 202 and is capable of flexing under pressure. In that regard, the pressure release valve 260 is suitable made from silicon or another flexible and compressible material. In the illustrated embodiment, the pressure release valve 260 includes a stem 264 and nub 266 for being received within and engaging with hole 262, as well as a flexible flap portion 268 that, when coupled to hole 262 is suitably positioned below the second housing portion 204 of the filtration assembly 228 to cover release holes 270 (see FIGS. 13 and 15).

During use, when the plunging assembly is being inserted into the outer container (see, e.g., FIG. 16A), water pressure maintains the pressure release valve 260 in a blocking position, to block any liquid entry through hole 262 or release holes 270. However, when the plunging assembly is being removed from the outer container (see, e.g., FIG. 16B), vacuum pressure causes the flap portion 268 to flex and extend downward creating a path through release holes 270 in the second housing portion 204 (see FIG. 15) which air or water may flow, as indicated by arrow A4, thereby releasing the vacuum pressure in the outer container 222. It should be appreciated that other venting mechanisms are also within the scope of the present disclosure, for example, one-way valve, release valve, and other mechanisms.

In the illustrated embodiment of FIGS. 13-16B, the filtration assembly 228 further includes an optional flapper valve 272 that can be used to prevent water in the inner sleeve from reentering the filtration assembly 228 after it has been filtered. The flapper valve 272 includes a stem 274 and an engagement portion 276 for engaging with hole 278 in the first housing portion 202. The flapper valve 272 further includes a flapper portion 280 for covering flow holes 282 in the first housing portion 202 (see FIGS. 13 and 14). When the plunging assembly is being inserted into the outer container (see, e.g., FIG. 16A), water pressure pushes against the flapper portion 280 of the flapper valve 272, causing the flapper portion 278 to flex and extend upward creating a path through flow holes 282 in the first housing portion 202, as indicated by arrow A3.

Further in the illustrated embodiment of FIGS. 13-16B, the first and second housing portions 202 and 204 snap fit together by engaging a plurality of fingers 284 extending downwardly from the first housing portion 202 into a plurality of holes 286 on the outer perimeter of the underside of the second housing portion 204. The holes 286 are large enough to also allow unfiltered water to flow through into the filtration assembly 228 when the plunging assembly is being inserted into the outer container (see, e.g., FIG. 16A).

Referring now to FIGS. 17-19, an alternate embodiment of a lid assembly will now be described. The lid assembly 330 of FIGS. 17-19 is substantially similar to the lid assembly 30 shown in FIGS. 6-11, except for differences regarding the drinking portion and the handle assembly of the lid assembly. Like numerals are used for the lid assembly 330 of FIGS. 17-19 as used for the lid assembly 30 of FIGS. 6-11 but in the 300 series.

Referring to FIGS. 17-19, the drinking portion 342 of the lid assembly 330 includes a substantially planar top exterior surface 331 that tilts from the drinking end 376 to the air hole end 370 when the filtration container assembly is in its upright orientation. The tilted surface 331 allows for water drainage into the drinking end 376 and provides a larger space for a user's nose during drinking. Compare the top exterior surface of the lid assembly 30 of FIGS. 6-11. In the illustrated embodiment of FIGS. 6-11, the top surface of the lid assembly 30 is substantially perpendicular to a longitudinal axis extending through the filtration container assembly 20 (see FIG. 1).

Referring to FIG. 18, the lock release 380 of the handle assembly 344 includes a biasing mechanism, shown as a spring 381, to bias the lock release 380 in the locked position.

Referring now to FIGS. 20-26, an alternate embodiment of a filtration assembly will now be described. The filtration assembly 428 of FIGS. 20-27 is substantially similar to the filtration assembly 28 of FIGS. 3 and 5, except for differences regarding the floating seal and the interface with the inner sleeve. Like numerals are used for the filtration assembly 428 of FIGS. 20-26 as used for the filtration assembly 28 of FIGS. 3 and 5, but in the 400 series.

As can be seen in the illustrated embodiment of FIGS. 21-24B, the filtration assembly 428 includes a filter housing having a first portion 402 and a second portion 404, filter media 406, first and second seals 412 and 414, and filter potting portions 408 and 410. As described in greater detail below, the filtration assembly 428 further includes a filter lock 460.

Figure 24A:
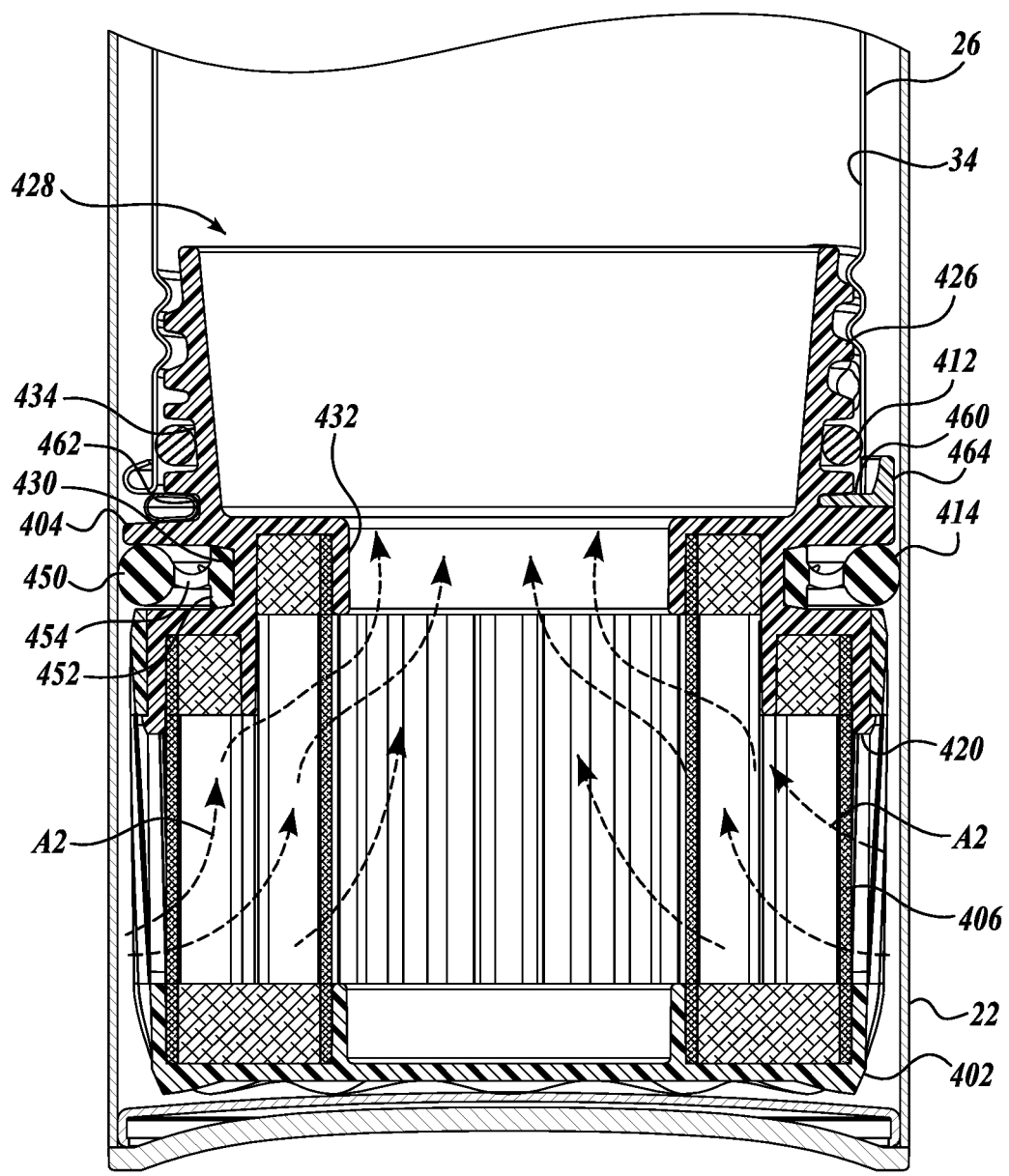

Extending from the first portion 402 is an upwardly extending threaded portion 426 for interfacing with threads 98 on the second end 54 of the inner sleeve 26 (see FIG. 23). Referring to FIG. 24A, the center hole 432 in the first portion 402 allows liquid to pass from holes 420 in the second portion 404 through the filter media 406 from the outer container 22 into the inner sleeve 26.

Groove 434 on first portion 402 is configured to receive the first seal 412 to form a seal with the inner wall 34 of the inner sleeve 26 when the filtration assembly 428 is coupled to the inner sleeve 26 (see FIG. 24A). In the illustrated embodiment, the first seal 412 is an o-ring type seal; however, other types of seals are also within the scope of the present disclosure.

Groove 430 on the first portion 404 is configured to receive the second seal 414. Because the groove 430 is sized to be slightly larger than the diameter of the second seal 414, the second seal 114 may be a "floating" seal that is movable between first "up" and second "down" positions (compare FIGS. 22A and 22B), as will be described in greater detail below. As compared to the floating seal 114 of FIGS. 3 and 5, the floating seal 414 of FIGS. 20-27 includes a floating portion 450 coupled to a non-floating portion 452, which are coupled to each other by a flexible coupling portion 454.

In the illustrated embodiment, the floating portion 450 is shown as an outer o-ring type seal, and the non-floating portion 452 is shown as an inner plug-type seal. The non-floating portion 452 nests in the annular groove 430 and prevents lateral movement of the seal 414. While the non-floating portion 452 prevents lateral movement, the floating portion 450 moves up and down to allow air, as indicated by arrow A1 in FIG. 24B, or water, as indicated by arrow A2 in FIG. 24A, to pass along the sides of the filtration assembly 428 between the filtration assembly 428 and the outer cup 22.

Figure 22:
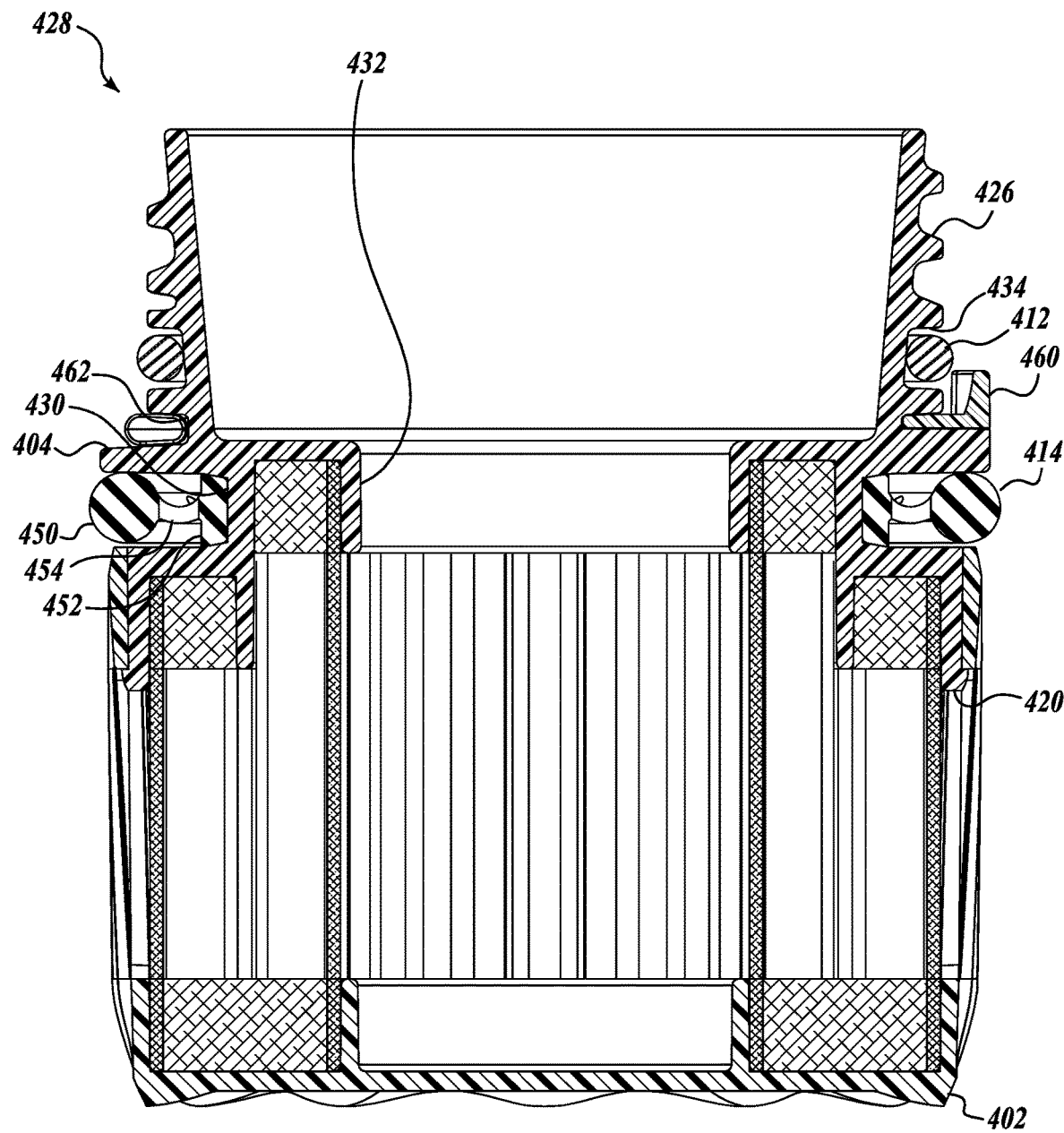
Figure 25:
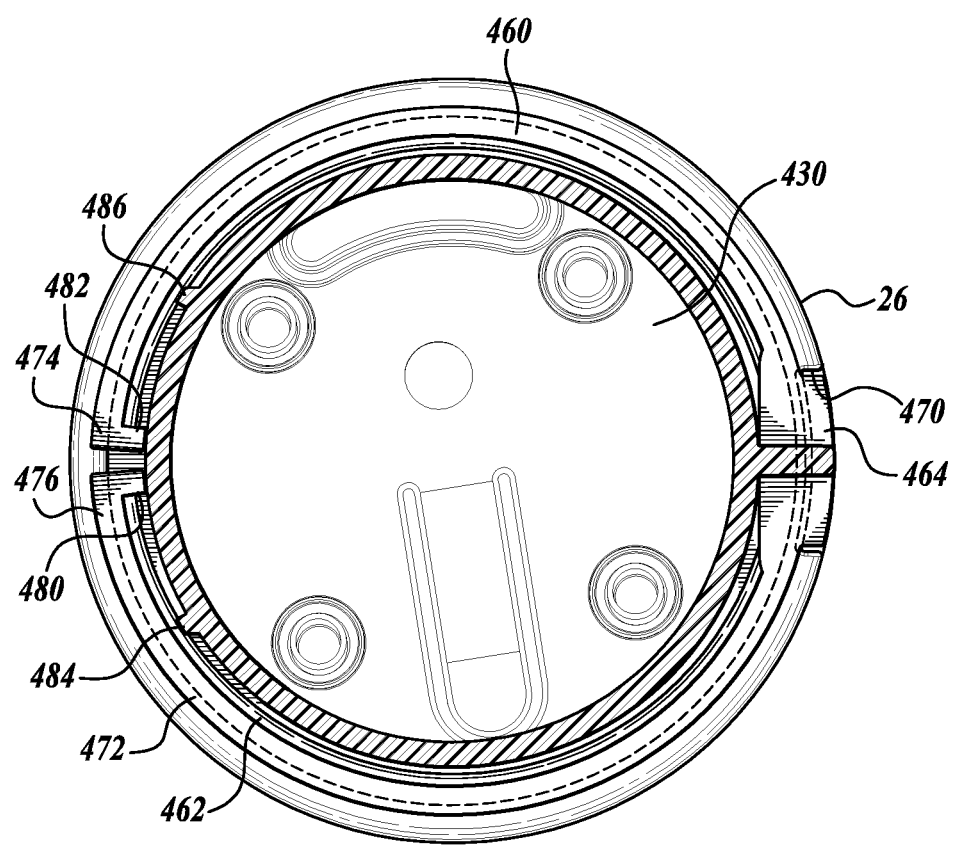
Figure 26:
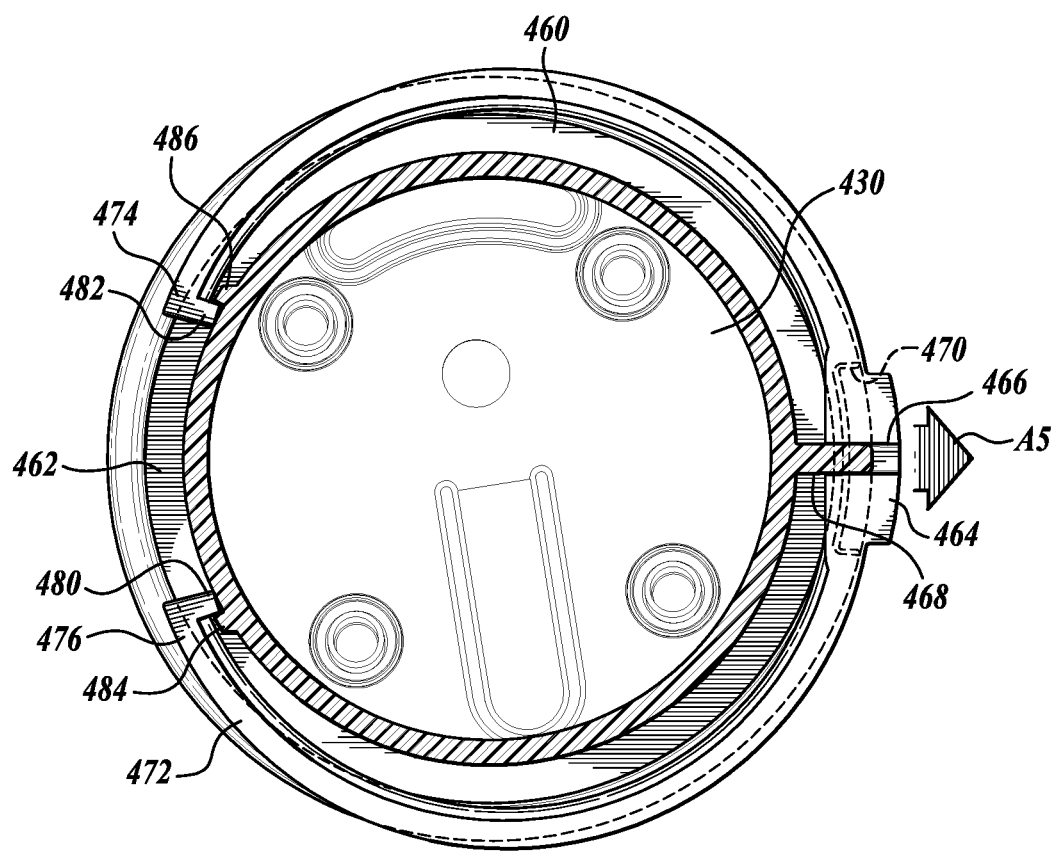
Figure 27:
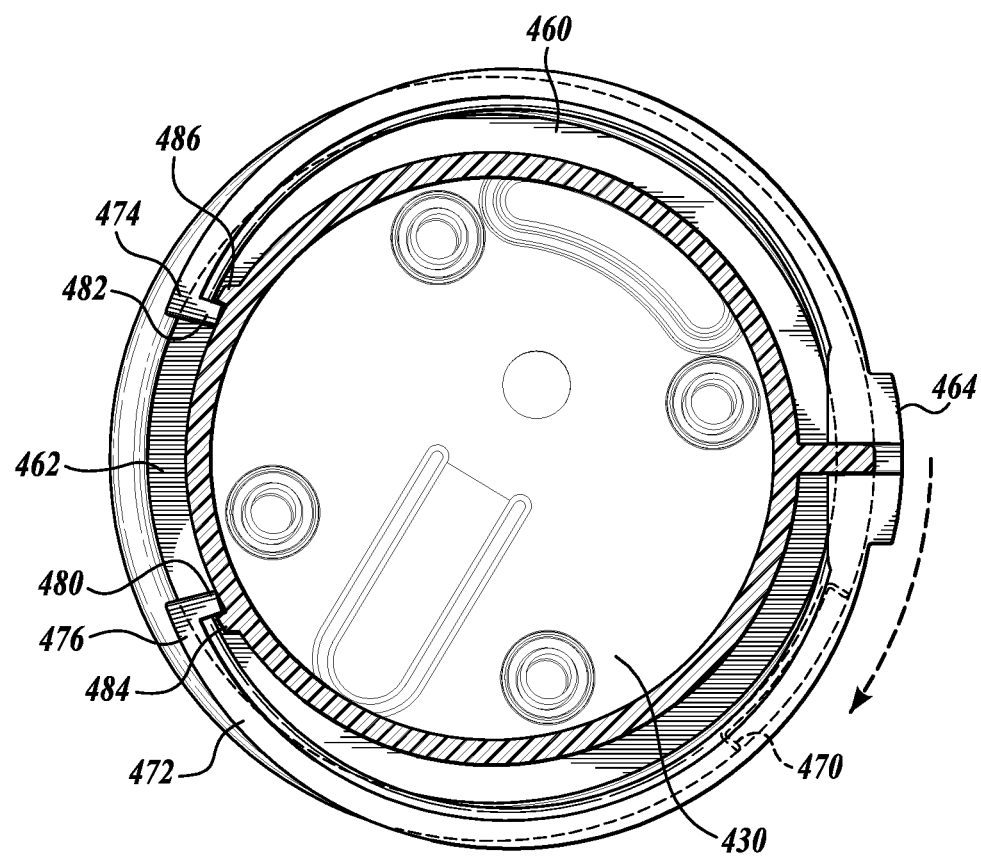

With reference to FIGS. 22, 23, and 25-27, the filter lock 460 will now be described in greater detail. The purpose of the filter lock 460 is to provide a locking mechanism between the filter assembly 428 and the inner sleeve 26. As can be seen in FIGS. 22 and 23, the filter lock 460 is received within an annular groove 462 on the filter assembly 428. Referring now to FIGS. 25-27, the filter lock 460 has a substantially C-shaped body 472. The filter lock 460 includes a user grip portion 464. Opposite the grip portion 464, the first and second ends 474 and 476 of the body portion 472 extend near to each other but are not joined. The filter lock 460 is manufactured from a plastic material or any other suitable material that can be deformed when subjected to force (see FIG. 26), and then can return to its normal position when the force is released (see FIG. 25).

Referring to FIGS. 22 and 23, when assembled, the filter lock 460 fits into groove 462 on the filter assembly 428. To prevent rotational movement of the filter lock 460 relative to the filter assembly 428, an interface is provided between the filter lock 460 and the groove 462. In the illustrated embodiment of FIG. 23, the filter lock 460 includes a groove 466 that receives and interfaces with a protrusion 468 extending from the groove 462 on the filter assembly 428.

Still referring to FIG. 23, when the filter assembly 428 (including the filter lock 460) is coupled with the inner sleeve 26, the user grip portion 464 is received within a detent 470 on the outer bottom perimeter of the inner sleeve 26.

Figure 24B:
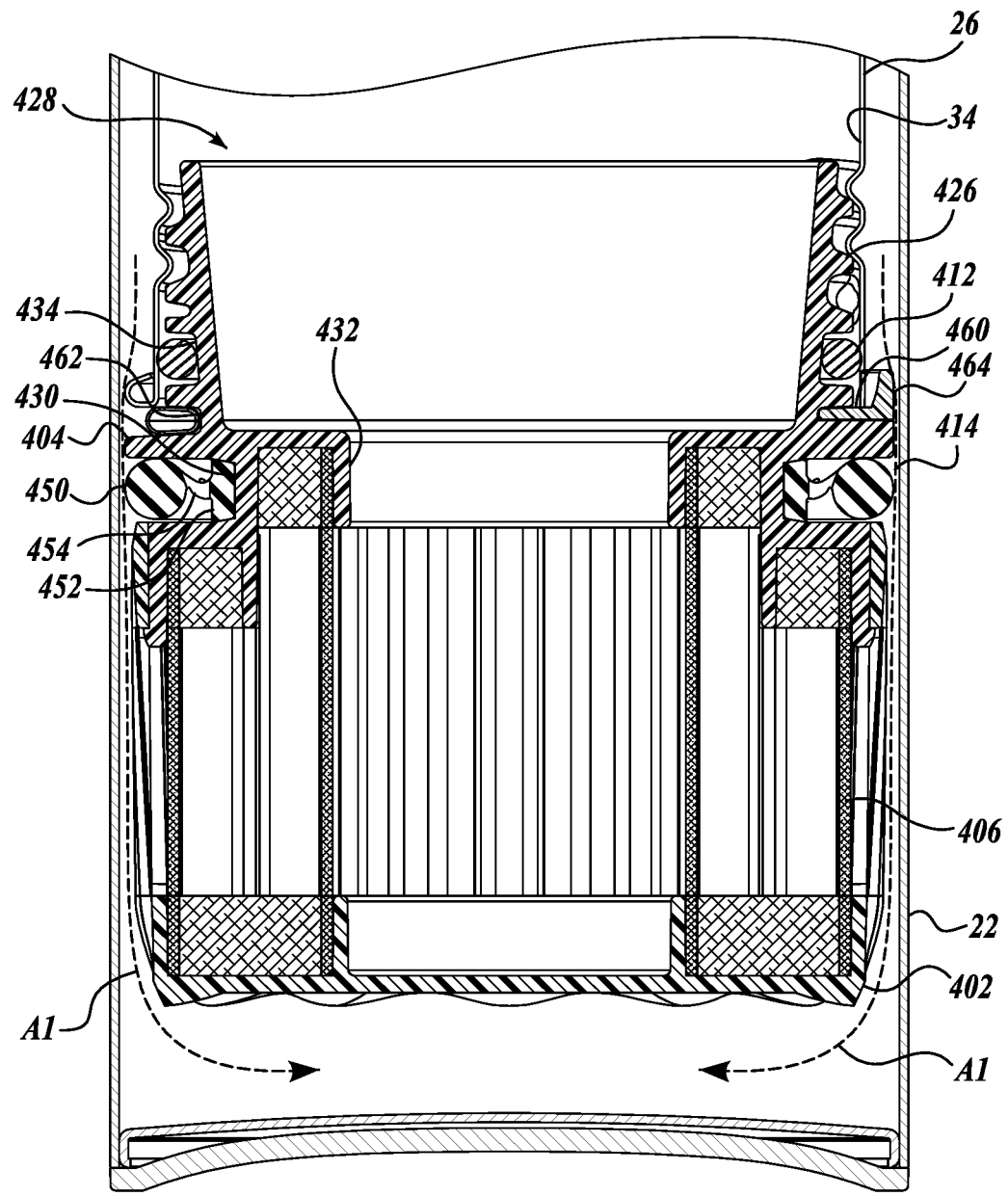

Referring to FIGS. 25-27, the movement of the filter lock 460 relative to the filter assembly 428 and the inner sleeve 26 will now be described. FIGS. 25-27 are cross sectional views of the filter assembly 428 coupled to the inner sleeve 26 looking up toward the lid assembly 430. Referring to FIG. 25, the filter lock 460 is in its locked position with the grip portion 464 received within the detent 470 on the outer bottom perimeter of the inner sleeve 26. Referring to FIGS. 24A and 24B, in this position, the grip portion 464 abuts the inner wall 34 of the outer sleeve 26 and prevents the filter assembly 428 from being removed from the inner sleeve 26. In this way, the filter assembly 428 is "locked" when the inner cup 26 is inserted into the outer cup 22, preventing accidental unthreading. The filter lock 460 thus provides a secure connection between the filter assembly 428 and the inner sleeve 26 during use of the container assembly.

Referring now to FIG. 26, the filter lock 460 is moved to its unlocked position, as indicated by arrow A5 showing movement of the grip portion 464. In the regard, the user would use a finger to pull the grip portion 464 of the filter lock 460 away from the outer surface of the inner sleeve 26. As the grip portion 464 is pulled, the groove 466 on the underside of the grip portion 464 travels along the protrusion 468 extending from the groove 462 on the filter assembly 428. In addition, the body portion 472 flexes such that the first and second ends 474 and 476 move away from each other and travel along the perimeter of the groove 462 on the filter assembly 428. As the body portion 472 flexes, stops 480 and 482 on the first and second ends 474 and 476 are designed to interface with protrusions 484 and 486 extending outwardly from the perimeter of the groove 462 on the filter assembly 428.

With the grip portion 464 pulled away from the outer surface of the inner sleeve 26, the locking engagement of the grip portion 464 with the detent 470 on the outer bottom perimeter of the inner sleeve 26 is released. Therefore, referring now to FIG. 27, when the locking engagement is released, the threads of the inner sleeve 26 can be rotated relative to the threads on the filter assembly 428.

While illustrative embodiments have been illustrated and described, it will be appreciated that various changes can be made therein without departing from the spirit and scope of the disclosure.

The embodiments of the disclosure in which an exclusive property or privilege is claimed are defined as follows:

1. A filtration container assembly, the assembly comprising:
   (a) an outer container having a first open end and a second closed end and defining an inner cavity; and
   (b) a plunging assembly having a first end and a second end configured to be received within the outer container inner cavity, wherein the plunging assembly includes an inner sleeve having a first end and a second end and an outer wall defining an inner bore, and a filtration assembly in fluid communication with the inner bore, the plunging assembly including a device for releasing pressure from the inner cavity of the outer container, the device for releasing pressure including a floating seal movable between first and second surfaces of the plunging assembly, the floating seal having a floating portion attached to a non-floating portion by a flexible coupling portion, wherein the floating portion is an o-ring seal, wherein the non-floating portion is coupled to the plunging assembly by nesting in an annular groove of the plunging assembly, and wherein the plunging assembly is configured to filter a liquid in the outer container as the liquid moves from the inner cavity of the outer container through the filtration assembly to the inner bore of the plunging assembly.

2. The filtration container assembly of claim 1, wherein the outer container has a substantially cylindrical outer wall defining the inner cavity.

3. The filtration container assembly of claim 1, wherein the inner sleeve has a substantially cylindrical outer wall.

4. The filtration container assembly of claim 1, wherein the inner cavity of the outer container and the inner sleeve of the plunging assembly are concentric with one another.

5. The filtration container assembly of claim 1, wherein the plunging assembly is configured to nest in the inner cavity of the outer container.

6. The filtration container assembly of claim 1, wherein the device for releasing pressure from the inner cavity of the outer container is located at or near the second end of the plunging assembly.

7. The filtration container assembly of claim 6, wherein the device for pressure release includes a pressure release valve.

8. The filtration container assembly of claim 6, wherein the device for pressure release is configured to maintain a seal when the plunging assembly is being inserted into the outer container.

9. The filtration container assembly of claim 8, wherein the device for pressure release is configured to release the seal when the plunging assembly is being removed from the outer container.

10. The filtration container assembly of claim 1, wherein the plunging assembly includes a collar assembly for interfacing with the outer container.

11. The filtration container assembly of claim 10, wherein the collar assembly is configured to create an interference fit between the plunging assembly and the outer container.

12. The filtration container assembly of claim 10, wherein the collar assembly includes a seal and a collar.

13. The filtration container assembly of claim 10, wherein the collar assembly is configured to engage with a plurality of depressions in the outer wall of the inner sleeve.

14. The filtration container assembly of claim 1, wherein the filtration assembly is releasably coupled to the inner sleeve at the second end.

15. The filtration container assembly of claim 1, wherein the filtration assembly and the inner sleeve are releasably coupled by a threaded connection.

16. The filtration container assembly of claim 1, wherein the outer wall of the inner sleeve is continuous from the first end to the second end.

17. The filtration container assembly of claim 1, wherein the cross-sectional area of the inner sleeve is substantially the same at the first end and the second end.

18. The filtration container assembly of claim 1, wherein the flexible couple portion extending between the floating portion and the non-floating portion of the floating seal has a length and a thickness, wherein the first end of the flexible coupling portion is coupled to the center portion of the non-floating portion, and wherein the thickness of the non-floating portion is greater than the thickness of the flexible coupling portion, and wherein the second end of the flexible coupling portion is coupled to the center portion of the floating portion, and wherein the thickness of the floating portion is greater than the thickness of the flexible coupling portion.

19. A method of filtering a liquid, the method comprising:
(a) obtaining an outer container having an inner cavity with a first open end and a second closed end and filling at least a portion of the outer container with the liquid;
(b) obtaining a plunging assembly having a first end and a second end configured to be received within the outer container inner cavity, wherein the plunging assembly includes an inner sleeve having a first end and a second end and an outer wall defining an inner bore, and a filtration assembly in fluid communication with the inner bore, the plunging assembly including a device for releasing pressure from the inner cavity of the outer container, the device for releasing pressure including a floating seal movable between first and second surfaces of the plunging assembly, the floating seal having a floating portion attached to a non-floating portion by a flexible coupling portion, wherein the floating portion is an o-ring seal, wherein the non-floating portion is coupled to the plunging assembly by nesting in an annular groove of the plunging assembly; and
(c) pressing the plunging assembly into the inner cavity of the outer container, such that the liquid flows from the inner cavity of the outer container through the filter and into the inner sleeve of the plunging assembly.

20. A filtration container assembly, the assembly comprising:
(a) an outer container having a first open end and a second closed end and defining an inner cavity; and
(b) a plunging assembly having a first end and a second end configured to be received within the outer container inner cavity, wherein the plunging assembly includes an inner sleeve having a first end and a second end and an outer wall defining an inner bore, and a filtration assembly in fluid communication with the inner bore, the plunging assembly including a device for releasing pressure from the inner cavity of the outer container, the device for releasing pressure including a floating seal movable between first and second surfaces of the plunging assembly, the floating seal having a floating portion attached to a non-floating portion by a flexible coupling portion, wherein the flexible couple portion extending between the floating portion and the non-floating portion of the floating seal has a length and a thickness, wherein the first end of the flexible coupling portion is coupled to the center portion of the non-floating portion, and wherein the thickness of the non-floating portion is greater than the thickness of the flexible coupling portion, and wherein the second end of the flexible coupling portion is coupled to the center portion of the floating portion, and wherein the thickness of the floating portion is greater than the thickness of the flexible coupling portion, and wherein the plunging assembly is configured to filter a liquid in the outer container as the liquid moves from the inner cavity of the outer container through the filtration assembly to the inner bore of the plunging assembly.

\* \* \* \* \*

UNITED STATES PATENT AND TRADEMARK OFFICE
CERTIFICATE OF CORRECTION

PATENT NO. : 11,179,657 B2
APPLICATION NO. : 16/927609
DATED : November 23, 2021
INVENTOR(S) : Nancie Weston, Travis Merrigan and Michael Bargiel Page 1 of 1

It is certified that error appears in the above-identified patent and that said Letters Patent is hereby corrected as shown below:

In the Claims

Column 15 Line 55 Claim 18, "the center portion" should read --a center portion--.

Column 16 Line 25 Claim 19, "the filter" should read --the filtration assembly--.

Signed and Sealed this
Fourth Day of October, 2022

Katherine Kelly Vidal
*Director of the United States Patent and Trademark Office*